(12) United States Patent
Vukicevic et al.

(10) Patent No.: US 7,572,440 B2
(45) Date of Patent: *Aug. 11, 2009

(54) METHOD FOR REPAIRING A DEFECT IN AN INTERVERTEBRAL DISC

(75) Inventors: Slobodan Vukicevic, Zagreb (HR); Vladimir Katic, Zagreb (HR); Kuber T. Sampath, Holliston, MA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/784,111

(22) Filed: Apr. 3, 2007

(65) Prior Publication Data

US 2008/0167225 A1 Jul. 10, 2008

Related U.S. Application Data

(60) Continuation of application No. 11/192,542, filed on Jul. 28, 2005, which is a division of application No. 09/828,607, filed on Apr. 6, 2001, now Pat. No. 6,958,149, which is a continuation of application No. PCT/US99/17222, filed on Jul. 30, 1999.

(51) Int. Cl.
*A61K 38/48* (2006.01)
(52) U.S. Cl. .................... 424/94.63; 424/93.7; 514/12; 514/2
(58) Field of Classification Search ........................ None
See application file for complete search history.

(56) References Cited

U.S. PATENT DOCUMENTS 6,958,149 B2 * 10/2005 Vukicevic et al. ......... 424/94.63
7,041,641 B2 * 5/2006 Rueger et al. .................. 514/12

FOREIGN PATENT DOCUMENTS

| WO | WO 95/16035 | 6/1995 |
| WO | WO 95/33502 | 12/1995 |
| WO | WO 96/14335 | 5/1996 |
| WO | WO 96/39170 | 12/1996 |
| WO | WO 98/31788 | 7/1998 |

OTHER PUBLICATIONS

Cui, P. C. et al., "Repair of thyroid cartilage defect with bone morphogenetic protein," Annals of Otology, Rhinology and Laryngology, 106(4), pp. 326-328 (1997).
Majstorovic, L. et al., "Biological repair of thyroid cartilage defects by osteogenic protein-1 (bone morphogenetic proteins-7) in dog," Bone (Abstract), 24(4), p. 419, abstract No. 42 (1999).
Vukicevic, S. et al., "Thyroid and articular cartilage repair in dog and sheep by OP-1," Bone (Abstracts), 24(4), p. 423, abstract No. 57 (1999).

* cited by examiner

*Primary Examiner*—Hope A Robinson
(74) *Attorney, Agent, or Firm*—Ropes & Gray LLP; James F. Haley, Jr.; Karen Mangasarian

(57) ABSTRACT

Provided herein are methods and devices for inducing the formation of functional replacement nonarticular cartilage tissues and ligament tissues. These methods and devices involve the use of osteogenic proteins, and are useful in repairing defects in the larynx, trachea, interarticular menisci, intervertebral discs, ear, nose, ribs and other fibrocartilaginous tissues in a mammal.

12 Claims, No Drawings

SEQUENCE LISTING

```
<160> NUMBER OF SEQ ID NOS: 9

<210> SEQ ID NO 1
<211> LENGTH: 1822
<212> TYPE: DNA
<213> ORGANISM: Homo sapiens
<220> FEATURE:
<221> NAME/KEY: CDS
<222> LOCATION: (49)..(1341)

<400> SEQUENCE: 1
ggtgcgggcc cggagcccgg agcccgggta gcgcgtagag ccggcgcg atg cac gtg         57
                                                    Met His Val
                                                      1 cgc tca ctg cga gct gcg gcg ccg cac agc ttc gtg gcg ctc tgg gca        105
Arg Ser Leu Arg Ala Ala Ala Pro His Ser Phe Val Ala Leu Trp Ala
      5                  10                  15 ccc ctg ttc ctg ctg cgc tcc gcc ctg gcc gac ttc agc ctg gac aac        153
Pro Leu Phe Leu Leu Arg Ser Ala Leu Ala Asp Phe Ser Leu Asp Asn
 20                  25                  30                  35 gag gtg cac tcg agc ttc atc cac cgg cgc ctc cgc agc cag gag cgg        201
Glu Val His Ser Ser Phe Ile His Arg Arg Leu Arg Ser Gln Glu Arg
                 40                  45                  50 cgg gag atg cag cgc gag atc ctc tcc att ttg ggc ttg ccc cac cgc        249
```

| | | |
|---|---|---|
| Arg Glu Met Gln Arg Glu Ile Leu Ser Ile Leu Gly Leu Pro His Arg<br>              55                    60                    65 | |
| ccg cgc ccg cac ctc cag ggc aag cac aac tcg gca ccc atg ttc atg<br>Pro Arg Pro His Leu Gln Gly Lys His Asn Ser Ala Pro Met Phe Met<br>        70                    75                    80 | 297 |
| ctg gac ctg tac aac gcc atg gcg gtg gag gag ggc ggc ggg ccc ggc<br>Leu Asp Leu Tyr Asn Ala Met Ala Val Glu Glu Gly Gly Gly Pro Gly<br>  85                      90                    95 | 345 |
| ggc cag ggc ttc tcc tac ccc tac aag gcc gtc ttc agt acc cag ggc<br>Gly Gln Gly Phe Ser Tyr Pro Tyr Lys Ala Val Phe Ser Thr Gln Gly<br>100                    105                 110               115 | 393 |
| ccc cct ctg gcc agc ctg caa gat agc cat ttc ctc acc gac gcc gac<br>Pro Pro Leu Ala Ser Leu Gln Asp Ser His Phe Leu Thr Asp Ala Asp<br>              120                 125               130 | 441 |
| atg gtc atg agc ttc gtc aac ctc gtg gaa cat gac aag gaa ttc ttc<br>Met Val Met Ser Phe Val Asn Leu Val Glu His Asp Lys Glu Phe Phe<br>            135                 140               145 | 489 |
| cac cca cgc tac cac cat cga gag ttc cgg ttt gat ctt tcc aag atc<br>His Pro Arg Tyr His His Arg Glu Phe Arg Phe Asp Leu Ser Lys Ile<br>        150                 155               160 | 537 |
| cca gaa ggg gaa gct gtc acg gca gcc gaa ttc cgg atc tac aag gac<br>Pro Glu Gly Glu Ala Val Thr Ala Ala Glu Phe Arg Ile Tyr Lys Asp<br>      165                 170               175 | 585 |
| tac atc cgg gaa cgc ttc gac aat gag acg ttc cgg atc agc gtt tat<br>Tyr Ile Arg Glu Arg Phe Asp Asn Glu Thr Phe Arg Ile Ser Val Tyr<br>180                    185                 190               195 | 633 |
| cag gtg ctc cag gag cac ttg ggc agg gaa tcg gat ctc ttc ctg ctc<br>Gln Val Leu Gln Glu His Leu Gly Arg Glu Ser Asp Leu Phe Leu Leu<br>              200                 205               210 | 681 |
| gac agc cgt acc ctc tgg gcc tcg gag gag ggc tgg ctg gtg ttt gac<br>Asp Ser Arg Thr Leu Trp Ala Ser Glu Glu Gly Trp Leu Val Phe Asp<br>            215                 220               225 | 729 |
| atc aca gcc acc agc aac cac tgg gtg gtc aat ccg cgg cac aac ctg<br>Ile Thr Ala Thr Ser Asn His Trp Val Val Asn Pro Arg His Asn Leu<br>        230                 235               240 | 777 |
| ggc ctg cag ctc tcg gtg gag acg ctg gat ggg cag agc atc aac ccc<br>Gly Leu Gln Leu Ser Val Glu Thr Leu Asp Gly Gln Ser Ile Asn Pro<br>      245                 250               255 | 825 |
| aag ttg gcg ggc ctg att ggg cgg cac ggg ccc cag aac aag cag ccc<br>Lys Leu Ala Gly Leu Ile Gly Arg His Gly Pro Gln Asn Lys Gln Pro<br>260                    265                 270               275 | 873 |
| ttc atg gtg gct ttc ttc aag gcc acg gag gtc cac ttc cgc agc atc<br>Phe Met Val Ala Phe Phe Lys Ala Thr Glu Val His Phe Arg Ser Ile<br>              280                 285               290 | 921 |
| cgg tcc acg ggg agc aaa cag cgc agc cag aac cgc tcc aag acg ccc<br>Arg Ser Thr Gly Ser Lys Gln Arg Ser Gln Asn Arg Ser Lys Thr Pro<br>            295                 300               305 | 969 |
| aag aac cag gaa gcc ctg cgg atg gcc aac gtg gca gag aac agc agc<br>Lys Asn Gln Glu Ala Leu Arg Met Ala Asn Val Ala Glu Asn Ser Ser<br>        310                 315               320 | 1017 |
| agc gac cag agg cag gcc tgt aag aag cac gag ctg tat gtc agc ttc<br>Ser Asp Gln Arg Gln Ala Cys Lys Lys His Glu Leu Tyr Val Ser Phe<br>      325                 330               335 | 1065 |
| cga gac ctg ggc tgg cag gac tgg atc atc gcg cct gaa ggc tac gcc<br>Arg Asp Leu Gly Trp Gln Asp Trp Ile Ile Ala Pro Glu Gly Tyr Ala<br>340                    345                 350               355 | 1113 |
| gcc tac tac tgt gag ggg gag tgt gcc ttc cct ctg aac tcc tac atg<br>Ala Tyr Tyr Cys Glu Gly Glu Cys Ala Phe Pro Leu Asn Ser Tyr Met<br>              360                 365               370 | 1161 |

```
aac gcc acc aac cac gcc atc gtg cag acg ctg gtc cac ttc atc aac    1209
Asn Ala Thr Asn His Ala Ile Val Gln Thr Leu Val His Phe Ile Asn
            375                 380                 385 ccg gaa acg gtg ccc aag ccc tgc tgt gcg ccc acg cag ctc aat gcc    1257
Pro Glu Thr Val Pro Lys Pro Cys Cys Ala Pro Thr Gln Leu Asn Ala
        390                 395                 400 atc tcc gtc ctc tac ttc gat gac agc tcc aac gtc atc ctg aag aaa    1305
Ile Ser Val Leu Tyr Phe Asp Asp Ser Ser Asn Val Ile Leu Lys Lys
405                 410                 415 tac aga aac atg gtg gtc cgg gcc tgt ggc tgc cac tagctcctcc         1351
Tyr Arg Asn Met Val Val Arg Ala Cys Gly Cys His
420                 425                 430 gagaattcag acccttggg gccaagtttt tctggatcct ccattgctcg ccttggccag   1411
gaaccagcag accaactgcc ttttgtgaga ccttccctc cctatcccca actttaaagg   1471
tgtgagagta ttaggaaaca tgagcagcat atggcttttg atcagttttt cagtggcagc  1531
atccaatgaa caagatccta caagctgtgc aggcaaaacc tagcaggaaa aaaaacaac   1591 gcataaagaa aaatggccgg gccaggtcat tggctgggaa gtctcagcca tgcacggact  1651
cgtttccaga ggtaattatg agcgcctacc agccaggcca cccagccgtg ggaggaaggg  1711
ggcgtggcaa ggggtgggca cattggtgtc tgtgcgaaag gaaaattgac ccggaagttc  1771
ctgtaataaa tgtcacaata aaacgaatga atgaaaaaaa aaaaaaaaaa a           1822

<210> SEQ ID NO 2
<211> LENGTH: 431
<212> TYPE: PRT
<213> ORGANISM: Homo sapiens

<400> SEQUENCE: 2

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205
```

```
Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
            275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 3
<211> LENGTH: 102
<212> TYPE: PRT
<213> ORGANISM: Artificial Sequence
<220> FEATURE:
<223> OTHER INFORMATION: Description of Artificial Sequence: Synthetic
      OPX amino acid sequence
<220> FEATURE:
<221> NAME/KEY: MOD_RES
<222> LOCATION: (2)
<223> OTHER INFORMATION: Lys or Arg
<220> FEATURE:
<221> NAME/KEY: MOD_RES
<222> LOCATION: (3)
<223> OTHER INFORMATION: Lys or Arg
<220> FEATURE:
<221> NAME/KEY: MOD_RES
<222> LOCATION: (11)
<223> OTHER INFORMATION: Arg or Gln
<220> FEATURE:
<221> NAME/KEY: MOD_RES
<222> LOCATION: (16)
<223> OTHER INFORMATION: Gln or Leu
<220> FEATURE:
<221> NAME/KEY: MOD_RES
<222> LOCATION: (19)
<223> OTHER INFORMATION: Ile or Val
<220> FEATURE:
<221> NAME/KEY: MOD_RES
<222> LOCATION: (23)
<223> OTHER INFORMATION: Glu or Gln
<220> FEATURE:
<221> NAME/KEY: MOD_RES
<222> LOCATION: (26)
<223> OTHER INFORMATION: Ala or Ser
<220> FEATURE:
```

```
<221> NAME/KEY: MOD_RES
<222> LOCATION: (35)
<223> OTHER INFORMATION: Ala or Ser
<220> FEATURE:
<221> NAME/KEY: MOD_RES
<222> LOCATION: (39)
<223> OTHER INFORMATION: Asn or Asp
<220> FEATURE:
<221> NAME/KEY: MOD_RES
<222> LOCATION: (41)
<223> OTHER INFORMATION: Tyr or Cys
<220> FEATURE:
<221> NAME/KEY: MOD_RES
<222> LOCATION: (50)
<223> OTHER INFORMATION: Val or Leu
<220> FEATURE:
<221> NAME/KEY: MOD_RES
<222> LOCATION: (52)
<223> OTHER INFORMATION: Ser or Thr
<220> FEATURE:
<221> NAME/KEY: MOD_RES
<222> LOCATION: (56)
<223> OTHER INFORMATION: Phe or Leu
<220> FEATURE:
<221> NAME/KEY: MOD_RES
<222> LOCATION: (57)
<223> OTHER INFORMATION: Ile or Met
<220> FEATURE:
<221> NAME/KEY: MOD_RES
<222> LOCATION: (58)
<223> OTHER INFORMATION: Asn or Lys
<220> FEATURE:
<221> NAME/KEY: MOD_RES
<222> LOCATION: (60)
<223> OTHER INFORMATION: Glu, Asp, or Asn
<220> FEATURE:
<221> NAME/KEY: MOD_RES
<222> LOCATION: (61)
<223> OTHER INFORMATION: Thr, Ala, or Val
<220> FEATURE:
<221> NAME/KEY: MOD_RES
<222> LOCATION: (65)
<223> OTHER INFORMATION: Pro or Ala
<220> FEATURE:
<221> NAME/KEY: MOD_RES
<222> LOCATION: (71)
<223> OTHER INFORMATION: Gln or Lys
<220> FEATURE:
<221> NAME/KEY: MOD_RES
<222> LOCATION: (73)
<223> OTHER INFORMATION: Asn or Ser
<220> FEATURE:
<221> NAME/KEY: MOD_RES
<222> LOCATION: (75)
<223> OTHER INFORMATION: Ile or Thr
<220> FEATURE:
<221> NAME/KEY: MOD_RES
<222> LOCATION: (80)
<223> OTHER INFORMATION: Phe or Tyr
<220> FEATURE:
<221> NAME/KEY: MOD_RES
<222> LOCATION: (82)
<223> OTHER INFORMATION: Asp or Ser
<220> FEATURE:
<221> NAME/KEY: MOD_RES
<222> LOCATION: (84)
<223> OTHER INFORMATION: Ser or Asn
<220> FEATURE:
<221> NAME/KEY: MOD_RES
<222> LOCATION: (89)
<223> OTHER INFORMATION: Lys or Arg
<220> FEATURE:
<221> NAME/KEY: MOD_RES
<222> LOCATION: (91)
<223> OTHER INFORMATION: Tyr or His
<220> FEATURE:
<221> NAME/KEY: MOD_RES
<222> LOCATION: (97)
<223> OTHER INFORMATION: Arg or Lys
```

<400> SEQUENCE: 3

Cys Xaa Xaa His Glu Leu Tyr Val Ser Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Ile Leu Xaa Lys Xaa Arg Asn Met Val Val
            85                  90                  95

Xaa Ala Cys Gly Cys His
            100

<210> SEQ ID NO 4
<211> LENGTH: 97
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (2)
<223> OTHER INFORMATION: Tyr or Lys
<220> FEATURE:
<221> NAME/KEY: MOD_RES
<222> LOCATION: (3)
<223> OTHER INFORMATION: Val or Ile
<220> FEATURE:
<221> NAME/KEY: MOD_RES
<222> LOCATION: (4)
<223> OTHER INFORMATION: Ser, Asp, or Glu
<220> FEATURE:
<221> NAME/KEY: MOD_RES
<222> LOCATION: (6)
<223> OTHER INFORMATION: Arg, Gln, Ser, Lys, or Ala
<220> FEATURE:
<221> NAME/KEY: MOD_RES
<222> LOCATION: (7)
<223> OTHER INFORMATION: Asp or Glu
<220> FEATURE:
<221> NAME/KEY: MOD_RES
<222> LOCATION: (8)
<223> OTHER INFORMATION: Leu, Val, or Ile
<220> FEATURE:
<221> NAME/KEY: MOD_RES
<222> LOCATION: (11)
<223> OTHER INFORMATION: Gln, Leu, Asp, His, Asn, or Ser
<220> FEATURE:
<221> NAME/KEY: MOD_RES
<222> LOCATION: (12)
<223> OTHER INFORMATION: Asp, Arg, Asn, or Glu
<220> FEATURE:
<221> NAME/KEY: MOD_RES
<222> LOCATION: (13)
<223> OTHER INFORMATION: Trp or Ser
<220> FEATURE:
<221> NAME/KEY: MOD_RES
<222> LOCATION: (14)
<223> OTHER INFORMATION: Ile or Val
<220> FEATURE:
<221> NAME/KEY: MOD_RES
<222> LOCATION: (15)
<223> OTHER INFORMATION: Ile or Val
<220> FEATURE:
<221> NAME/KEY: MOD_RES
<222> LOCATION: (16)

-continued

```
<223> OTHER INFORMATION: Ala or Ser
<220> FEATURE:
<221> NAME/KEY: MOD_RES
<222> LOCATION: (18)
<223> OTHER INFORMATION: Glu, Gln, Leu, Lys, Pro, or Arg
<220> FEATURE:
<221> NAME/KEY: MOD_RES
<222> LOCATION: (19)
<223> OTHER INFORMATION: Gly or Ser
<220> FEATURE:
<221> NAME/KEY: MOD_RES
<222> LOCATION: (20)
<223> OTHER INFORMATION: Tyr or Phe
<220> FEATURE:
<221> NAME/KEY: MOD_RES
<222> LOCATION: (21)
<223> OTHER INFORMATION: Ala, Ser, Asp, Met, His, Gln, Leu, or Gly
<220> FEATURE:
<221> NAME/KEY: MOD_RES
<222> LOCATION: (23)
<223> OTHER INFORMATION: Tyr, Asn, or Phe
<220> FEATURE:
<221> NAME/KEY: MOD_RES
<222> LOCATION: (26)
<223> OTHER INFORMATION: Glu, His, Tyr, Asp, Gln, Ala, or Ser
<220> FEATURE:
<221> NAME/KEY: MOD_RES
<222> LOCATION: (28)
<223> OTHER INFORMATION: Glu, Lys, Asp, Gln, or Ala
<220> FEATURE:
<221> NAME/KEY: MOD_RES
<222> LOCATION: (30)
<223> OTHER INFORMATION: Ala, Ser, Pro, Gln, Ile, or Asn
<220> FEATURE:
<221> NAME/KEY: MOD_RES
<222> LOCATION: (31)
<223> OTHER INFORMATION: Phe, Leu, or Tyr
<220> FEATURE:
<221> NAME/KEY: MOD_RES
<222> LOCATION: (33)
<223> OTHER INFORMATION: Leu, Val, or Met
<220> FEATURE:
<221> NAME/KEY: MOD_RES
<222> LOCATION: (34)
<223> OTHER INFORMATION: Asn, Asp, Ala, Thr, or Pro
<220> FEATURE:
<221> NAME/KEY: MOD_RES
<222> LOCATION: (35)
<223> OTHER INFORMATION: Ser, Asp, Glu, Leu, Ala, or Lys
<220> FEATURE:
<221> NAME/KEY: MOD_RES
<222> LOCATION: (36)
<223> OTHER INFORMATION: Tyr, Cys, His, Ser, or Ile
<220> FEATURE:
<221> NAME/KEY: MOD_RES
<222> LOCATION: (37)
<223> OTHER INFORMATION: Met, Phe, Gly, or Leu
<220> FEATURE:
<221> NAME/KEY: MOD_RES
<222> LOCATION: (38)
<223> OTHER INFORMATION: Asn, Ser, or Lys
<220> FEATURE:
<221> NAME/KEY: MOD_RES
<222> LOCATION: (39)
<223> OTHER INFORMATION: Ala, Ser, Gly, or Pro
<220> FEATURE:
<221> NAME/KEY: MOD_RES
<222> LOCATION: (40)
<223> OTHER INFORMATION: Thr, Leu, or Ser
<220> FEATURE:
<221> NAME/KEY: MOD_RES
<222> LOCATION: (44)
<223> OTHER INFORMATION: Ile, Val, or Thr
<220> FEATURE:
<221> NAME/KEY: MOD_RES
<222> LOCATION: (45)
<223> OTHER INFORMATION: Val, Leu, Met, or Ile
<220> FEATURE:
<221> NAME/KEY: MOD_RES
```

```
<222> LOCATION: (46)
<223> OTHER INFORMATION: Gln or Arg
<220> FEATURE:
<221> NAME/KEY: MOD_RES
<222> LOCATION: (47)
<223> OTHER INFORMATION: Thr, Ala, or Ser
<220> FEATURE:
<221> NAME/KEY: MOD_RES
<222> LOCATION: (48)
<223> OTHER INFORMATION: Leu or Ile
<220> FEATURE:
<221> NAME/KEY: MOD_RES
<222> LOCATION: (49)
<223> OTHER INFORMATION: Val or Met
<220> FEATURE:
<221> NAME/KEY: MOD_RES
<222> LOCATION: (50)
<223> OTHER INFORMATION: His, Asn, or Arg
<220> FEATURE:
<221> NAME/KEY: MOD_RES
<222> LOCATION: (51)
<223> OTHER INFORMATION: Phe, Leu, Asn, Ser, Ala, or Val
<220> FEATURE:
<221> NAME/KEY: MOD_RES
<222> LOCATION: (52)
<223> OTHER INFORMATION: Ile, Met, Asn, Ala, Val, Gly, or Leu
<220> FEATURE:
<221> NAME/KEY: MOD_RES
<222> LOCATION: (53)
<223> OTHER INFORMATION: Asn, Lys, Ala, Glu, Gly, or Phe
<220> FEATURE:
<221> NAME/KEY: MOD_RES
<222> LOCATION: (54)
<223> OTHER INFORMATION: Pro, Ser, or Val
<220> FEATURE:
<221> NAME/KEY: MOD_RES
<222> LOCATION: (55)
<223> OTHER INFORMATION: Glu, Asp, Asn, Gly, Val, Pro, or Lys
<220> FEATURE:
<221> NAME/KEY: MOD_RES
<222> LOCATION: (56)
<223> OTHER INFORMATION: Thr, Ala, Val, Lys, Asp, Tyr, Ser, Gly, Ile,
      or His
<220> FEATURE:
<221> NAME/KEY: MOD_RES
<222> LOCATION: (57)
<223> OTHER INFORMATION: Val, Ala, or Ile
<220> FEATURE:
<221> NAME/KEY: MOD_RES
<222> LOCATION: (58)
<223> OTHER INFORMATION: Pro or Asp
<220> FEATURE:
<221> NAME/KEY: MOD_RES
<222> LOCATION: (59)
<223> OTHER INFORMATION: Lys, Leu, or Glu
<220> FEATURE:
<221> NAME/KEY: MOD_RES
<222> LOCATION: (60)
<223> OTHER INFORMATION: Pro, Val, or Ala
<220> FEATURE:
<221> NAME/KEY: MOD_RES
<222> LOCATION: (63)
<223> OTHER INFORMATION: Ala or Val
<220> FEATURE:
<221> NAME/KEY: MOD_RES
<222> LOCATION: (65)
<223> OTHER INFORMATION: Thr, Ala, or Glu
<220> FEATURE:
<221> NAME/KEY: MOD_RES
<222> LOCATION: (66)
<223> OTHER INFORMATION: Gln, Lys, Arg, or Glu
<220> FEATURE:
<221> NAME/KEY: MOD_RES
<222> LOCATION: (67)
<223> OTHER INFORMATION: Leu, Met, or Val
<220> FEATURE:
<221> NAME/KEY: MOD_RES
<222> LOCATION: (68)
<223> OTHER INFORMATION: Asn, Ser, Asp, or Gly
```

-continued

```
<220> FEATURE:
<221> NAME/KEY: MOD_RES
<222> LOCATION: (69)
<223> OTHER INFORMATION: Ala, Pro, or Ser
<220> FEATURE:
<221> NAME/KEY: MOD_RES
<222> LOCATION: (70)
<223> OTHER INFORMATION: Ile, Thr, Val, or Leu
<220> FEATURE:
<221> NAME/KEY: MOD_RES
<222> LOCATION: (71)
<223> OTHER INFORMATION: Ser, Ala, or Pro
<220> FEATURE:
<221> NAME/KEY: MOD_RES
<222> LOCATION: (72)
<223> OTHER INFORMATION: Val, Leu, Met, or Ile
<220> FEATURE:
<221> NAME/KEY: MOD_RES
<222> LOCATION: (74)
<223> OTHER INFORMATION: Tyr or Phe
<220> FEATURE:
<221> NAME/KEY: MOD_RES
<222> LOCATION: (75)
<223> OTHER INFORMATION: Phe, Tyr, Leu, or His
<220> FEATURE:
<221> NAME/KEY: MOD_RES
<222> LOCATION: (76)
<223> OTHER INFORMATION: Asp, Asn, or Leu
<220> FEATURE:
<221> NAME/KEY: MOD_RES
<222> LOCATION: (77)
<223> OTHER INFORMATION: Asp, Glu, Asn, Arg, or Ser
<220> FEATURE:
<221> NAME/KEY: MOD_RES
<222> LOCATION: (78)
<223> OTHER INFORMATION: Ser, Gln, Asn, Tyr, or Asp
<220> FEATURE:
<221> NAME/KEY: MOD_RES
<222> LOCATION: (79)
<223> OTHER INFORMATION: Ser, Asn, Asp, Glu, or Lys
<220> FEATURE:
<221> NAME/KEY: MOD_RES
<222> LOCATION: (80)
<223> OTHER INFORMATION: Asn, Thr, or Lys
<220> FEATURE:
<221> NAME/KEY: MOD_RES
<222> LOCATION: (82)
<223> OTHER INFORMATION: Ile, Val, or Asn
<220> FEATURE:
<221> NAME/KEY: MOD_RES
<222> LOCATION: (84)
<223> OTHER INFORMATION: Lys or Arg
<220> FEATURE:
<221> NAME/KEY: MOD_RES
<222> LOCATION: (85)
<223> OTHER INFORMATION: Lys, Asn, Gln, His, Arg, or Val
<220> FEATURE:
<221> NAME/KEY: MOD_RES
<222> LOCATION: (86)
<223> OTHER INFORMATION: Tyr, Glu, or His
<220> FEATURE:
<221> NAME/KEY: MOD_RES
<222> LOCATION: (87)
<223> OTHER INFORMATION: Arg, Gln, Glu, or Pro
<220> FEATURE:
<221> NAME/KEY: MOD_RES
<222> LOCATION: (88)
<223> OTHER INFORMATION: Asn, Glu, Trp, or Asp
<220> FEATURE:
<221> NAME/KEY: MOD_RES
<222> LOCATION: (90)
<223> OTHER INFORMATION: Val, Thr, Ala, or Ile
<220> FEATURE:
<221> NAME/KEY: MOD_RES
<222> LOCATION: (92)
<223> OTHER INFORMATION: Arg, Lys, Val, Asp, Gln, or Glu
<220> FEATURE:
<221> NAME/KEY: MOD_RES
<222> LOCATION: (93)
```

```
<223> OTHER INFORMATION: Ala, Gly, Glu, or Ser
<220> FEATURE:
<221> NAME/KEY: MOD_RES
<222> LOCATION: (95)
<223> OTHER INFORMATION: Gly or Ala
<220> FEATURE:
<221> NAME/KEY: MOD_RES
<222> LOCATION: (97)
<223> OTHER INFORMATION: His or Arg

<400> SEQUENCE: 4

Leu Xaa Xaa Xaa Phe Xaa Xaa Xaa Gly Trp Xaa Xaa Xaa Xaa Xaa
1               5                   10                  15

Pro Xaa Xaa Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Xaa
        35                  40                  45

Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
            85                  90                  95

Xaa

<210> SEQ ID NO 5
<211> LENGTH: 102
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (2)
<223> OTHER INFORMATION: Lys, Arg, Ala, or Gln
<220> FEATURE:
<221> NAME/KEY: MOD_RES
<222> LOCATION: (3)
<223> OTHER INFORMATION: Lys, Arg, or Met
<220> FEATURE:
<221> NAME/KEY: MOD_RES
<222> LOCATION: (4)
<223> OTHER INFORMATION: His, Arg, or Gln
<220> FEATURE:
<221> NAME/KEY: MOD_RES
<222> LOCATION: (5)
<223> OTHER INFORMATION: Glu, Ser, His, Gly, Arg, Pro, Thr, or Tyr
<220> FEATURE:
<221> NAME/KEY: MOD_RES
<222> LOCATION: (7)
<223> OTHER INFORMATION: Tyr or Lys
<220> FEATURE:
<221> NAME/KEY: MOD_RES
<222> LOCATION: (8)
<223> OTHER INFORMATION: Val or Ile
<220> FEATURE:
<221> NAME/KEY: MOD_RES
<222> LOCATION: (9)
<223> OTHER INFORMATION: Ser, Asp, or Glu
<220> FEATURE:
<221> NAME/KEY: MOD_RES
<222> LOCATION: (11)
<223> OTHER INFORMATION: Arg, Gln, Ser, Lys, or Ala
<220> FEATURE:
<221> NAME/KEY: MOD_RES
<222> LOCATION: (12)
<223> OTHER INFORMATION: Asp or Glu
<220> FEATURE:
<221> NAME/KEY: MOD_RES
<222> LOCATION: (13)
```

```
<223> OTHER INFORMATION: Leu, Val, or Ile
<220> FEATURE:
<221> NAME/KEY: MOD_RES
<222> LOCATION: (16)
<223> OTHER INFORMATION: Gln, Leu, Asp, His, Asn, or Ser
<220> FEATURE:
<221> NAME/KEY: MOD_RES
<222> LOCATION: (17)
<223> OTHER INFORMATION: Asp, Arg, Asn, or Glu
<220> FEATURE:
<221> NAME/KEY: MOD_RES
<222> LOCATION: (18)
<223> OTHER INFORMATION: Trp or Ser
<220> FEATURE:
<221> NAME/KEY: MOD_RES
<222> LOCATION: (19)
<223> OTHER INFORMATION: Ile or Val
<220> FEATURE:
<221> NAME/KEY: MOD_RES
<222> LOCATION: (20)
<223> OTHER INFORMATION: Ile or Val
<220> FEATURE:
<221> NAME/KEY: MOD_RES
<222> LOCATION: (21)
<223> OTHER INFORMATION: Ala or Ser
<220> FEATURE:
<221> NAME/KEY: MOD_RES
<222> LOCATION: (23)
<223> OTHER INFORMATION: Glu, Gln, Leu, Lys, Pro, or Arg
<220> FEATURE:
<221> NAME/KEY: MOD_RES
<222> LOCATION: (24)
<223> OTHER INFORMATION: Gly or Ser
<220> FEATURE:
<221> NAME/KEY: MOD_RES
<222> LOCATION: (25)
<223> OTHER INFORMATION: Tyr or Phe
<220> FEATURE:
<221> NAME/KEY: MOD_RES
<222> LOCATION: (26)
<223> OTHER INFORMATION: Ala, Ser, Asp, Met, His, Gln, Leu, or Gly
<220> FEATURE:
<221> NAME/KEY: MOD_RES
<222> LOCATION: (28)
<223> OTHER INFORMATION: Tyr, Asn, or Phe
<220> FEATURE:
<221> NAME/KEY: MOD_RES
<222> LOCATION: (31)
<223> OTHER INFORMATION: Glu, His, Tyr, Asp, Gln, Ala, or Ser
<220> FEATURE:
<221> NAME/KEY: MOD_RES
<222> LOCATION: (33)
<223> OTHER INFORMATION: Glu, Lys, Asp, Gln, or Ala
<220> FEATURE:
<221> NAME/KEY: MOD_RES
<222> LOCATION: (35)
<223> OTHER INFORMATION: Ala, Ser, Pro, Gln, Ile, or Asn
<220> FEATURE:
<221> NAME/KEY: MOD_RES
<222> LOCATION: (36)
<223> OTHER INFORMATION: Phe, Leu, or Tyr
<220> FEATURE:
<221> NAME/KEY: MOD_RES
<222> LOCATION: (38)
<223> OTHER INFORMATION: Leu, Val, or Met
<220> FEATURE:
<221> NAME/KEY: MOD_RES
<222> LOCATION: (39)
<223> OTHER INFORMATION: Asn, Asp, Ala, Thr, or Pro
<220> FEATURE:
<221> NAME/KEY: MOD_RES
<222> LOCATION: (40)
<223> OTHER INFORMATION: Ser, Asp, Glu, Leu, Ala, or Lys
<220> FEATURE:
<221> NAME/KEY: MOD_RES
<222> LOCATION: (41)
<223> OTHER INFORMATION: Tyr, Cys, His, Ser, or Ile
<220> FEATURE:
<221> NAME/KEY: MOD_RES
```

-continued

```
<222> LOCATION: (42)
<223> OTHER INFORMATION: Met, Phe, Gly, or Leu
<220> FEATURE:
<221> NAME/KEY: MOD_RES
<222> LOCATION: (43)
<223> OTHER INFORMATION: Asn, Ser, or Lys
<220> FEATURE:
<221> NAME/KEY: MOD_RES
<222> LOCATION: (44)
<223> OTHER INFORMATION: Ala, Ser, Gly, or Pro
<220> FEATURE:
<221> NAME/KEY: MOD_RES
<222> LOCATION: (45)
<223> OTHER INFORMATION: Thr, Leu, or Ser
<220> FEATURE:
<221> NAME/KEY: MOD_RES
<222> LOCATION: (49)
<223> OTHER INFORMATION: Ile, Val, or Thr
<220> FEATURE:
<221> NAME/KEY: MOD_RES
<222> LOCATION: (50)
<223> OTHER INFORMATION: Val, Leu, Met, or Ile
<220> FEATURE:
<221> NAME/KEY: MOD_RES
<222> LOCATION: (51)
<223> OTHER INFORMATION: Gln or Arg
<220> FEATURE:
<221> NAME/KEY: MOD_RES
<222> LOCATION: (52)
<223> OTHER INFORMATION: Thr, Ala, or Ser
<220> FEATURE:
<221> NAME/KEY: MOD_RES
<222> LOCATION: (53)
<223> OTHER INFORMATION: Leu or Ile
<220> FEATURE:
<221> NAME/KEY: MOD_RES
<222> LOCATION: (54)
<223> OTHER INFORMATION: Val or Met
<220> FEATURE:
<221> NAME/KEY: MOD_RES
<222> LOCATION: (55)
<223> OTHER INFORMATION: His, Asn, or Arg
<220> FEATURE:
<221> NAME/KEY: MOD_RES
<222> LOCATION: (56)
<223> OTHER INFORMATION: Phe, Leu, Asn, Ser, Ala, or Val
<220> FEATURE:
<221> NAME/KEY: MOD_RES
<222> LOCATION: (57)
<223> OTHER INFORMATION: Ile, Met, Asn, Ala, Val, Gly, or Leu
<220> FEATURE:
<221> NAME/KEY: MOD_RES
<222> LOCATION: (58)
<223> OTHER INFORMATION: Asn, Lys, Ala, Glu, Gly, or Phe
<220> FEATURE:
<221> NAME/KEY: MOD_RES
<222> LOCATION: (59)
<223> OTHER INFORMATION: Pro, Ser, or Val
<220> FEATURE:
<221> NAME/KEY: MOD_RES
<222> LOCATION: (60)
<223> OTHER INFORMATION: Glu, Asp, Asn, Gly, Val, Pro, or Lys
<220> FEATURE:
<221> NAME/KEY: MOD_RES
<222> LOCATION: (61)
<223> OTHER INFORMATION: Thr, Ala, Val, Lys, Asp, Tyr, Ser, Gly, Ile,
      or His
<220> FEATURE:
<221> NAME/KEY: MOD_RES
<222> LOCATION: (62)
<223> OTHER INFORMATION: Val, Ala, or Ile
<220> FEATURE:
<221> NAME/KEY: MOD_RES
<222> LOCATION: (63)
<223> OTHER INFORMATION: Pro or Asp
<220> FEATURE:
<221> NAME/KEY: MOD_RES
<222> LOCATION: (64)
<223> OTHER INFORMATION: Lys, Leu, or Glu
```

```
<220> FEATURE:
<221> NAME/KEY: MOD_RES
<222> LOCATION: (65)
<223> OTHER INFORMATION: Pro, Val, or Ala
<220> FEATURE:
<221> NAME/KEY: MOD_RES
<222> LOCATION: (68)
<223> OTHER INFORMATION: Ala or Val
<220> FEATURE:
<221> NAME/KEY: MOD_RES
<222> LOCATION: (70)
<223> OTHER INFORMATION: Thr, Ala, or Glu
<220> FEATURE:
<221> NAME/KEY: MOD_RES
<222> LOCATION: (71)
<223> OTHER INFORMATION: Gln, Lys, Arg, or Glu
<220> FEATURE:
<221> NAME/KEY: MOD_RES
<222> LOCATION: (72)
<223> OTHER INFORMATION: Leu, Met, or Val
<220> FEATURE:
<221> NAME/KEY: MOD_RES
<222> LOCATION: (73)
<223> OTHER INFORMATION: Asn, Ser, Asp, or Gly
<220> FEATURE:
<221> NAME/KEY: MOD_RES
<222> LOCATION: (74)
<223> OTHER INFORMATION: Ala, Pro, or Ser
<220> FEATURE:
<221> NAME/KEY: MOD_RES
<222> LOCATION: (75)
<223> OTHER INFORMATION: Ile, Thr, Val, or Leu
<220> FEATURE:
<221> NAME/KEY: MOD_RES
<222> LOCATION: (76)
<223> OTHER INFORMATION: Ser, Ala, or Pro
<220> FEATURE:
<221> NAME/KEY: MOD_RES
<222> LOCATION: (77)
<223> OTHER INFORMATION: Val, Leu, Met, or Ile
<220> FEATURE:
<221> NAME/KEY: MOD_RES
<222> LOCATION: (79)
<223> OTHER INFORMATION: Tyr or Phe
<220> FEATURE:
<221> NAME/KEY: MOD_RES
<222> LOCATION: (80)
<223> OTHER INFORMATION: Phe, Tyr, Leu, or His
<220> FEATURE:
<221> NAME/KEY: MOD_RES
<222> LOCATION: (81)
<223> OTHER INFORMATION: Asp, Asn, or Leu
<220> FEATURE:
<221> NAME/KEY: MOD_RES
<222> LOCATION: (82)
<223> OTHER INFORMATION: Asp, Glu, Asn, Arg, or Ser
<220> FEATURE:
<221> NAME/KEY: MOD_RES
<222> LOCATION: (83)
<223> OTHER INFORMATION: Ser, Gln, Asn, Tyr, or Asp
<220> FEATURE:
<221> NAME/KEY: MOD_RES
<222> LOCATION: (84)
<223> OTHER INFORMATION: Ser, Asn, Asp, Glu, or Lys
<220> FEATURE:
<221> NAME/KEY: MOD_RES
<222> LOCATION: (85)
<223> OTHER INFORMATION: Asn, Thr, or Lys
<220> FEATURE:
<221> NAME/KEY: MOD_RES
<222> LOCATION: (87)
<223> OTHER INFORMATION: Ile, Val, or Asn
<220> FEATURE:
<221> NAME/KEY: MOD_RES
<222> LOCATION: (89)
<223> OTHER INFORMATION: Lys or Arg
<220> FEATURE:
<221> NAME/KEY: MOD_RES
<222> LOCATION: (90)
```

```
<223> OTHER INFORMATION: Lys, Asn, Gln, His, Arg, or Val
<220> FEATURE:
<221> NAME/KEY: MOD_RES
<222> LOCATION: (91)
<223> OTHER INFORMATION: Tyr, Glu, or His
<220> FEATURE:
<221> NAME/KEY: MOD_RES
<222> LOCATION: (92)
<223> OTHER INFORMATION: Arg, Gln, Glu, or Pro
<220> FEATURE:
<221> NAME/KEY: MOD_RES
<222> LOCATION: (93)
<223> OTHER INFORMATION: Asn, Glu, Trp, or Asp
<220> FEATURE:
<221> NAME/KEY: MOD_RES
<222> LOCATION: (95)
<223> OTHER INFORMATION: Val, Thr, Ala, or Ile
<220> FEATURE:
<221> NAME/KEY: MOD_RES
<222> LOCATION: (97)
<223> OTHER INFORMATION: Arg, Lys, Val, Asp, Gln, or Glu
<220> FEATURE:
<221> NAME/KEY: MOD_RES
<222> LOCATION: (98)
<223> OTHER INFORMATION: Ala, Gly, Glu, or Ser
<220> FEATURE:
<221> NAME/KEY: MOD_RES
<222> LOCATION: (100)
<223> OTHER INFORMATION: Gly or Ala
<220> FEATURE:
<221> NAME/KEY: MOD_RES
<222> LOCATION: (102)
<223> OTHER INFORMATION: His or Arg

<400> SEQUENCE: 5

Cys Xaa Xaa Xaa Xaa Leu Xaa Xaa Xaa Phe Xaa Xaa Xaa Gly Trp Xaa
1               5                   10                  15

Xaa Xaa Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Xaa Cys Xaa
            100

<210> SEQ ID NO 6
<211> LENGTH: 97
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Phe, Leu, or Glu
<220> FEATURE:
<221> NAME/KEY: MOD_RES
<222> LOCATION: (2)
<223> OTHER INFORMATION: Tyr, Phe, His, Arg, Thr, Lys, Gln, Val, or Glu
<220> FEATURE:
<221> NAME/KEY: MOD_RES
<222> LOCATION: (3)
<223> OTHER INFORMATION: Val, Ile, Leu, or Asp
<220> FEATURE:
<221> NAME/KEY: MOD_RES
```

```
<222> LOCATION: (4)
<223> OTHER INFORMATION: Ser, Asp, Glu, Asn, or Phe
<220> FEATURE:
<221> NAME/KEY: MOD_RES
<222> LOCATION: (5)
<223> OTHER INFORMATION: Phe or Glu
<220> FEATURE:
<221> NAME/KEY: MOD_RES
<222> LOCATION: (6)
<223> OTHER INFORMATION: Arg, Gln, Lys, Ser, Glu, Ala, or Asn
<220> FEATURE:
<221> NAME/KEY: MOD_RES
<222> LOCATION: (7)
<223> OTHER INFORMATION: Asp, Glu, Leu, Ala, or Gln
<220> FEATURE:
<221> NAME/KEY: MOD_RES
<222> LOCATION: (8)
<223> OTHER INFORMATION: Leu, Val, Met, Ile, or Phe
<220> FEATURE:
<221> NAME/KEY: MOD_RES
<222> LOCATION: (9)
<223> OTHER INFORMATION: Gly, His, or Lys
<220> FEATURE:
<221> NAME/KEY: MOD_RES
<222> LOCATION: (10)
<223> OTHER INFORMATION: Trp or Met
<220> FEATURE:
<221> NAME/KEY: MOD_RES
<222> LOCATION: (11)
<223> OTHER INFORMATION: Gln, Leu, His, Glu, Asn, Asp, Ser, or Gly
<220> FEATURE:
<221> NAME/KEY: MOD_RES
<222> LOCATION: (12)
<223> OTHER INFORMATION: Asp, Asn, Ser, Lys, Arg, Glu, or His
<220> FEATURE:
<221> NAME/KEY: MOD_RES
<222> LOCATION: (13)
<223> OTHER INFORMATION: Trp or Ser
<220> FEATURE:
<221> NAME/KEY: MOD_RES
<222> LOCATION: (14)
<223> OTHER INFORMATION: Ile or Val
<220> FEATURE:
<221> NAME/KEY: MOD_RES
<222> LOCATION: (15)
<223> OTHER INFORMATION: Ile or Val
<220> FEATURE:
<221> NAME/KEY: MOD_RES
<222> LOCATION: (16)
<223> OTHER INFORMATION: Ala, Ser, Tyr, or Trp
<220> FEATURE:
<221> NAME/KEY: MOD_RES
<222> LOCATION: (18)
<223> OTHER INFORMATION: Glu, Lys, Gln, Met, Pro, Leu, Arg, His, or Lys
<220> FEATURE:
<221> NAME/KEY: MOD_RES
<222> LOCATION: (19)
<223> OTHER INFORMATION: Gly, Glu, Asp, Lys, Ser, Gln, Arg, or Phe
<220> FEATURE:
<221> NAME/KEY: MOD_RES
<222> LOCATION: (20)
<223> OTHER INFORMATION: Tyr or Phe
<220> FEATURE:
<221> NAME/KEY: MOD_RES
<222> LOCATION: (21)
<223> OTHER INFORMATION: Ala, Ser, Gly, Met, Gln, His, Glu, Asp, Leu,
      Asn, Lys, or Thr
<220> FEATURE:
<221> NAME/KEY: MOD_RES
<222> LOCATION: (22)
<223> OTHER INFORMATION: Ala or Pro
<220> FEATURE:
<221> NAME/KEY: MOD_RES
<222> LOCATION: (23)
<223> OTHER INFORMATION: Tyr, Phe, Asn, Ala, or Arg
<220> FEATURE:
<221> NAME/KEY: MOD_RES
<222> LOCATION: (24)
<223> OTHER INFORMATION: Tyr, His, Glu, Phe, or Arg
```

```
<220> FEATURE:
<221> NAME/KEY: MOD_RES
<222> LOCATION: (26)
<223> OTHER INFORMATION: Glu, Asp, Ala, Ser, Tyr, His, Lys, Arg, Gln,
      or Gly
<220> FEATURE:
<221> NAME/KEY: MOD_RES
<222> LOCATION: (28)
<223> OTHER INFORMATION: Glu, Asp, Leu, Val, Lys, Gly, Thr, Ala, or Gln
<220> FEATURE:
<221> NAME/KEY: MOD_RES
<222> LOCATION: (30)
<223> OTHER INFORMATION: Ala, Ser, Ile, Asn, Pro, Glu, Asp, Phe, Gln,
      or Leu
<220> FEATURE:
<221> NAME/KEY: MOD_RES
<222> LOCATION: (31)
<223> OTHER INFORMATION: Phe, Tyr, Leu, Asn, Gly, or Arg
<220> FEATURE:
<221> NAME/KEY: MOD_RES
<222> LOCATION: (32)
<223> OTHER INFORMATION: Pro, Ser, Ala, or Val
<220> FEATURE:
<221> NAME/KEY: MOD_RES
<222> LOCATION: (33)
<223> OTHER INFORMATION: Leu, Met, Glu, Phe, or Val
<220> FEATURE:
<221> NAME/KEY: MOD_RES
<222> LOCATION: (34)
<223> OTHER INFORMATION: Asn, Asp, Thr, Gly, Ala, Arg, Leu, or Pro
<220> FEATURE:
<221> NAME/KEY: MOD_RES
<222> LOCATION: (35)
<223> OTHER INFORMATION: Ser, Ala, Glu, Asp, Thr, Leu, Lys, Gln, or His
<220> FEATURE:
<221> NAME/KEY: MOD_RES
<222> LOCATION: (36)
<223> OTHER INFORMATION: Tyr, His, Cys, Ile, Arg, Asp, Asn, Lys, Ser,
      Glu, or Gly
<220> FEATURE:
<221> NAME/KEY: MOD_RES
<222> LOCATION: (37)
<223> OTHER INFORMATION: Met, Leu, Phe, Val, Gly, or Tyr
<220> FEATURE:
<221> NAME/KEY: MOD_RES
<222> LOCATION: (38)
<223> OTHER INFORMATION: Asn, Glu, Thr, Pro, Lys, His, Gly, Met, Val,
      or Arg
<220> FEATURE:
<221> NAME/KEY: MOD_RES
<222> LOCATION: (39)
<223> OTHER INFORMATION: Ala, Ser, Gly, Pro, or Phe
<220> FEATURE:
<221> NAME/KEY: MOD_RES
<222> LOCATION: (40)
<223> OTHER INFORMATION: Thr, Ser, Leu, Pro, His, or Met
<220> FEATURE:
<221> NAME/KEY: MOD_RES
<222> LOCATION: (41)
<223> OTHER INFORMATION: Asn, Lys, Val, Thr, or Gln
<220> FEATURE:
<221> NAME/KEY: MOD_RES
<222> LOCATION: (42)
<223> OTHER INFORMATION: His, Tyr, or Lys
<220> FEATURE:
<221> NAME/KEY: MOD_RES
<222> LOCATION: (43)
<223> OTHER INFORMATION: Ala, Thr, Leu, or Tyr
<220> FEATURE:
<221> NAME/KEY: MOD_RES
<222> LOCATION: (44)
<223> OTHER INFORMATION: Ile, Thr, Val, Phe, Tyr, Met, or Pro
<220> FEATURE:
<221> NAME/KEY: MOD_RES
<222> LOCATION: (45)
<223> OTHER INFORMATION: Val, Leu, Met, Ile, or His
<220> FEATURE:
<221> NAME/KEY: MOD_RES
<222> LOCATION: (46)
```

```
<223> OTHER INFORMATION: Gln, Arg, or Thr
<220> FEATURE:
<221> NAME/KEY: MOD_RES
<222> LOCATION: (47)
<223> OTHER INFORMATION: Thr, Ser, Ala, Asn, or His
<220> FEATURE:
<221> NAME/KEY: MOD_RES
<222> LOCATION: (48)
<223> OTHER INFORMATION: Leu, Asn, or Ile
<220> FEATURE:
<221> NAME/KEY: MOD_RES
<222> LOCATION: (49)
<223> OTHER INFORMATION: Val, Met, Leu, Pro, or Ile
<220> FEATURE:
<221> NAME/KEY: MOD_RES
<222> LOCATION: (50)
<223> OTHER INFORMATION: His, Asn, Arg, Lys, Tyr, or Gln
<220> FEATURE:
<221> NAME/KEY: MOD_RES
<222> LOCATION: (51)
<223> OTHER INFORMATION: Phe, Leu, Ser, Asn, Met, Ala, Arg, Glu, Gly,
      or Gln
<220> FEATURE:
<221> NAME/KEY: MOD_RES
<222> LOCATION: (52)
<223> OTHER INFORMATION: Ile, Met, Leu, Val, Lys, Gln, Ala, or Tyr
<220> FEATURE:
<221> NAME/KEY: MOD_RES
<222> LOCATION: (53)
<223> OTHER INFORMATION: Asn, Phe, Lys, Glu, Asp, Ala, Gln, Gly, Leu,
      or Val
<220> FEATURE:
<221> NAME/KEY: MOD_RES
<222> LOCATION: (54)
<223> OTHER INFORMATION: Pro, Asn, Ser, Val, or Asp
<220> FEATURE:
<221> NAME/KEY: MOD_RES
<222> LOCATION: (55)
<223> OTHER INFORMATION: Glu, Asp, Asn, Lys, Arg, Ser, Gly, Thr, Gln,
      Pro, or His
<220> FEATURE:
<221> NAME/KEY: MOD_RES
<222> LOCATION: (56)
<223> OTHER INFORMATION: Thr, His, Tyr, Ala, Ile, Lys, Asp, Ser, Gly,
      or Arg
<220> FEATURE:
<221> NAME/KEY: MOD_RES
<222> LOCATION: (57)
<223> OTHER INFORMATION: Val, Ile, Thr, Ala, Leu, or Ser
<220> FEATURE:
<221> NAME/KEY: MOD_RES
<222> LOCATION: (58)
<223> OTHER INFORMATION: Pro, Gly, Ser, Asp, or Ala
<220> FEATURE:
<221> NAME/KEY: MOD_RES
<222> LOCATION: (59)
<223> OTHER INFORMATION: Lys, Leu, Pro, Ala, Ser, Glu, Arg, or Gly
<220> FEATURE:
<221> NAME/KEY: MOD_RES
<222> LOCATION: (60)
<223> OTHER INFORMATION: Pro, Ala, Val, Thr, or Ser
<220> FEATURE:
<221> NAME/KEY: MOD_RES
<222> LOCATION: (61)
<223> OTHER INFORMATION: Cys, Val, or Ser
<220> FEATURE:
<221> NAME/KEY: MOD_RES
<222> LOCATION: (63)
<223> OTHER INFORMATION: Ala, Val, or Thr
<220> FEATURE:
<221> NAME/KEY: MOD_RES
<222> LOCATION: (65)
<223> OTHER INFORMATION: Thr, Ala, Glu, Val, Gly, Asp, or Tyr
<220> FEATURE:
<221> NAME/KEY: MOD_RES
<222> LOCATION: (66)
<223> OTHER INFORMATION: Gln, Lys, Glu, Arg, or Val
<220> FEATURE:
<221> NAME/KEY: MOD_RES
```

-continued

```
<222> LOCATION: (67)
<223> OTHER INFORMATION: Leu, Met, Thr, or Tyr
<220> FEATURE:
<221> NAME/KEY: MOD_RES
<222> LOCATION: (68)
<223> OTHER INFORMATION: Asn, Ser, Gly, Thr, Asp, Glu, Lys, or Val
<220> FEATURE:
<221> NAME/KEY: MOD_RES
<222> LOCATION: (69)
<223> OTHER INFORMATION: Ala, Pro, Gly, or Ser
<220> FEATURE:
<221> NAME/KEY: MOD_RES
<222> LOCATION: (70)
<223> OTHER INFORMATION: Ile, Thr, Leu, or Val
<220> FEATURE:
<221> NAME/KEY: MOD_RES
<222> LOCATION: (71)
<223> OTHER INFORMATION: Ser, Pro, Ala, Thr, Asn, or Gly
<220> FEATURE:
<221> NAME/KEY: MOD_RES
<222> LOCATION: (72)
<223> OTHER INFORMATION: Val, Ile, Leu, or Met
<220> FEATURE:
<221> NAME/KEY: MOD_RES
<222> LOCATION: (74)
<223> OTHER INFORMATION: Tyr, Phe, Arg, Thr, Tyr, or Met
<220> FEATURE:
<221> NAME/KEY: MOD_RES
<222> LOCATION: (75)
<223> OTHER INFORMATION: Phe, Tyr, His, Leu, Ile, Lys, Gln, or Val
<220> FEATURE:
<221> NAME/KEY: MOD_RES
<222> LOCATION: (76)
<223> OTHER INFORMATION: Asp, Leu, Asn, or Glu
<220> FEATURE:
<221> NAME/KEY: MOD_RES
<222> LOCATION: (77)
<223> OTHER INFORMATION: Asp, Ser, Arg, Asn, Glu, Ala, Lys, Gly, or Pro
<220> FEATURE:
<221> NAME/KEY: MOD_RES
<222> LOCATION: (78)
<223> OTHER INFORMATION: Ser, Asn, Asp, Tyr, Ala, Gly, Gln, Met, Glu,
      Asn, or Lys
<220> FEATURE:
<221> NAME/KEY: MOD_RES
<222> LOCATION: (79)
<223> OTHER INFORMATION: Ser, Asn, Glu, Asp, Val, Lys, Gly, Gln, or Arg
<220> FEATURE:
<221> NAME/KEY: MOD_RES
<222> LOCATION: (80)
<223> OTHER INFORMATION: Asn, Lys, Thr, Pro, Val, Ile, Arg, Ser, or Gln
<220> FEATURE:
<221> NAME/KEY: MOD_RES
<222> LOCATION: (81)
<223> OTHER INFORMATION: Val, Ile, Thr, or Ala
<220> FEATURE:
<221> NAME/KEY: MOD_RES
<222> LOCATION: (82)
<223> OTHER INFORMATION: Ile, Asn, Val, Leu, Tyr, Asp, or Ala
<220> FEATURE:
<221> NAME/KEY: MOD_RES
<222> LOCATION: (83)
<223> OTHER INFORMATION: Leu, Tyr, Lys, or Ile
<220> FEATURE:
<221> NAME/KEY: MOD_RES
<222> LOCATION: (84)
<223> OTHER INFORMATION: Lys, Arg, Asn, Tyr, Phe, Thr, Glu, or Gly
<220> FEATURE:
<221> NAME/KEY: MOD_RES
<222> LOCATION: (85)
<223> OTHER INFORMATION: Lys, Arg, His, Gln, Asn, Glu, or Val
<220> FEATURE:
<221> NAME/KEY: MOD_RES
<222> LOCATION: (86)
<223> OTHER INFORMATION: Tyr, His, Glu, or Ile
<220> FEATURE:
<221> NAME/KEY: MOD_RES
<222> LOCATION: (87)
<223> OTHER INFORMATION: Arg, Glu, Gln, Pro, or Lys
```

```
<220> FEATURE:
<221> NAME/KEY: MOD_RES
<222> LOCATION: (88)
<223> OTHER INFORMATION: Asn, Asp, Ala, Glu, Gly, or Lys
<220> FEATURE:
<221> NAME/KEY: MOD_RES
<222> LOCATION: (89)
<223> OTHER INFORMATION: Met or Ala
<220> FEATURE:
<221> NAME/KEY: MOD_RES
<222> LOCATION: (90)
<223> OTHER INFORMATION: Val, Ile, Ala, Thr, Ser, or Lys
<220> FEATURE:
<221> NAME/KEY: MOD_RES
<222> LOCATION: (91)
<223> OTHER INFORMATION: Val or Ala
<220> FEATURE:
<221> NAME/KEY: MOD_RES
<222> LOCATION: (92)
<223> OTHER INFORMATION: Arg, Lys, Gln, Asp, Glu, Val, Ala, Ser, or Thr
<220> FEATURE:
<221> NAME/KEY: MOD_RES
<222> LOCATION: (93)
<223> OTHER INFORMATION: Ala, Ser, Glu, Gly, Arg, or Thr
<220> FEATURE:
<221> NAME/KEY: MOD_RES
<222> LOCATION: (95)
<223> OTHER INFORMATION: Gly, Ala, or Thr
<220> FEATURE:
<221> NAME/KEY: MOD_RES
<222> LOCATION: (97)
<223> OTHER INFORMATION: His, Arg, Gly, Leu, or Ser

<400> SEQUENCE: 6

Xaa Xaa Xaa Xaa Xaa Xaa Xaa Xaa Xaa Xaa Xaa Xaa Xaa Xaa Xaa
1               5                   10                  15

Pro Xaa Xaa Xaa Xaa Xaa Xaa Xaa Cys Xaa Gly Xaa Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Xaa Pro
    50                  55                  60

Xaa Xaa Xaa Xaa Xaa Xaa Xaa Xaa Leu Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
            85                  90                  95

Xaa

<210> SEQ ID NO 7
<211> LENGTH: 102
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (2)
<223> OTHER INFORMATION: Lys, Arg, Gln, Ser, His, Glu, Ala, or Cys
<220> FEATURE:
<221> NAME/KEY: MOD_RES
<222> LOCATION: (3)
<223> OTHER INFORMATION: Lys, Arg, Met, Lys, Thr, Leu, Tyr, or Ala
<220> FEATURE:
<221> NAME/KEY: MOD_RES
<222> LOCATION: (4)
<223> OTHER INFORMATION: His, Gln, Arg, Lys, Thr, Leu, Val, Pro, or Tyr
<220> FEATURE:
<221> NAME/KEY: MOD_RES
<222> LOCATION: (5)
<223> OTHER INFORMATION: Gln, Thr, His, Arg, Pro, Ser, Ala, Gln, Asn,
```

Tyr, Lys, Asp, or Leu
<220> FEATURE:
<221> NAME/KEY: MOD_RES
<222> LOCATION: (6)
<223> OTHER INFORMATION: Phe, Leu, or Glu
<220> FEATURE:
<221> NAME/KEY: MOD_RES
<222> LOCATION: (7)
<223> OTHER INFORMATION: Tyr, Phe, His, Arg, Thr, Lys, Gln, Val, or Glu
<220> FEATURE:
<221> NAME/KEY: MOD_RES
<222> LOCATION: (8)
<223> OTHER INFORMATION: Val, Ile, Leu, or Asp
<220> FEATURE:
<221> NAME/KEY: MOD_RES
<222> LOCATION: (9)
<223> OTHER INFORMATION: Ser, Asp, Glu, Asn, or Phe
<220> FEATURE:
<221> NAME/KEY: MOD_RES
<222> LOCATION: (10)
<223> OTHER INFORMATION: Phe or Glu
<220> FEATURE:
<221> NAME/KEY: MOD_RES
<222> LOCATION: (11)
<223> OTHER INFORMATION: Arg, Gln, Lys, Ser, Glu, Ala, or Asn
<220> FEATURE:
<221> NAME/KEY: MOD_RES
<222> LOCATION: (12)
<223> OTHER INFORMATION: Asp, Glu, Leu, Ala, or Gln
<220> FEATURE:
<221> NAME/KEY: MOD_RES
<222> LOCATION: (13)
<223> OTHER INFORMATION: Leu, Val, Met, Ile, or Phe
<220> FEATURE:
<221> NAME/KEY: MOD_RES
<222> LOCATION: (14)
<223> OTHER INFORMATION: Gly, His, or Lys
<220> FEATURE:
<221> NAME/KEY: MOD_RES
<222> LOCATION: (15)
<223> OTHER INFORMATION: Trp or Met
<220> FEATURE:
<221> NAME/KEY: MOD_RES
<222> LOCATION: (16)
<223> OTHER INFORMATION: Gln, Leu, His, Glu, Asn, Asp, Ser, or Gly
<220> FEATURE:
<221> NAME/KEY: MOD_RES
<222> LOCATION: (17)
<223> OTHER INFORMATION: Asp, Asn, Ser, Lys, Arg, Glu, or His
<220> FEATURE:
<221> NAME/KEY: MOD_RES
<222> LOCATION: (18)
<223> OTHER INFORMATION: Trp or Ser
<220> FEATURE:
<221> NAME/KEY: MOD_RES
<222> LOCATION: (19)
<223> OTHER INFORMATION: Ile or Val
<220> FEATURE:
<221> NAME/KEY: MOD_RES
<222> LOCATION: (20)
<223> OTHER INFORMATION: Ile or Val
<220> FEATURE:
<221> NAME/KEY: MOD_RES
<222> LOCATION: (21)
<223> OTHER INFORMATION: Ala, Ser, Tyr, or Trp
<220> FEATURE:
<221> NAME/KEY: MOD_RES
<222> LOCATION: (23)
<223> OTHER INFORMATION: Glu, Lys, Gln, Met, Pro, Leu, Arg, His, or Lys
<220> FEATURE:
<221> NAME/KEY: MOD_RES
<222> LOCATION: (24)
<223> OTHER INFORMATION: Gly, Glu, Asp, Lys, Ser, Gln, Arg, or Phe
<220> FEATURE:
<221> NAME/KEY: MOD_RES
<222> LOCATION: (25)
<223> OTHER INFORMATION: Tyr or Phe
<220> FEATURE:
<221> NAME/KEY: MOD_RES

```
<222> LOCATION: (26)
<223> OTHER INFORMATION: Ala, Ser, Gly, Met, Gln, His, Glu, Asp, Leu,
      Asn, Lys, or Thr
<220> FEATURE:
<221> NAME/KEY: MOD_RES
<222> LOCATION: (27)
<223> OTHER INFORMATION: Ala or Pro
<220> FEATURE:
<221> NAME/KEY: MOD_RES
<222> LOCATION: (28)
<223> OTHER INFORMATION: Tyr, Phe, Asn, Ala, or Arg
<220> FEATURE:
<221> NAME/KEY: MOD_RES
<222> LOCATION: (29)
<223> OTHER INFORMATION: Tyr, His, Glu, Phe, or Arg
<220> FEATURE:
<221> NAME/KEY: MOD_RES
<222> LOCATION: (31)
<223> OTHER INFORMATION: Glu, Asp, Ala, Ser, Tyr, His, Lys, Arg, Gln,
      or Gly
<220> FEATURE:
<221> NAME/KEY: MOD_RES
<222> LOCATION: (33)
<223> OTHER INFORMATION: Glu, Asp, Leu, Val, Lys, Gly, Thr, Ala, or Gln
<220> FEATURE:
<221> NAME/KEY: MOD_RES
<222> LOCATION: (35)
<223> OTHER INFORMATION: Ala, Ser, Ile, Asn, Pro, Glu, Asp, Phe, Gln,
      or Leu
<220> FEATURE:
<221> NAME/KEY: MOD_RES
<222> LOCATION: (36)
<223> OTHER INFORMATION: Phe, Tyr, Leu, Asn, Gly, or Arg
<220> FEATURE:
<221> NAME/KEY: MOD_RES
<222> LOCATION: (37)
<223> OTHER INFORMATION: Pro, Ser, Ala, or Val
<220> FEATURE:
<221> NAME/KEY: MOD_RES
<222> LOCATION: (38)
<223> OTHER INFORMATION: Leu, Met, Glu, Phe, or Val
<220> FEATURE:
<221> NAME/KEY: MOD_RES
<222> LOCATION: (39)
<223> OTHER INFORMATION: Asn, Asp, Thr, Gly, Ala, Arg, Leu, or Pro
<220> FEATURE:
<221> NAME/KEY: MOD_RES
<222> LOCATION: (40)
<223> OTHER INFORMATION: Ser, Ala, Glu, Asp, Thr, Leu, Lys, Gln, or His
<220> FEATURE:
<221> NAME/KEY: MOD_RES
<222> LOCATION: (41)
<223> OTHER INFORMATION: Tyr, His, Cys, Ile, Arg, Asp, Asn, Lys, Ser,
      Glu, or Gly
<220> FEATURE:
<221> NAME/KEY: MOD_RES
<222> LOCATION: (42)
<223> OTHER INFORMATION: Met, Leu, Phe, Val, Gly, or Tyr
<220> FEATURE:
<221> NAME/KEY: MOD_RES
<222> LOCATION: (43)
<223> OTHER INFORMATION: Asn, Glu, Thr, Pro, Lys, His, Gly, Met, Val,
      or Arg
<220> FEATURE:
<221> NAME/KEY: MOD_RES
<222> LOCATION: (44)
<223> OTHER INFORMATION: Ala, Ser, Gly, Pro, or Phe
<220> FEATURE:
<221> NAME/KEY: MOD_RES
<222> LOCATION: (45)
<223> OTHER INFORMATION: Thr, Ser, Leu, Pro, His, or Met
<220> FEATURE:
<221> NAME/KEY: MOD_RES
<222> LOCATION: (46)
<223> OTHER INFORMATION: Asn, Lys, Val, Thr, or Gln
<220> FEATURE:
<221> NAME/KEY: MOD_RES
<222> LOCATION: (47)
<223> OTHER INFORMATION: His, Tyr, or Lys
```

-continued

```
<220> FEATURE:
<221> NAME/KEY: MOD_RES
<222> LOCATION: (48)
<223> OTHER INFORMATION: Ala, Thr, Leu, or Tyr
<220> FEATURE:
<221> NAME/KEY: MOD_RES
<222> LOCATION: (49)
<223> OTHER INFORMATION: Ile, Thr, Val, Phe, Tyr, Met, or Pro
<220> FEATURE:
<221> NAME/KEY: MOD_RES
<222> LOCATION: (50)
<223> OTHER INFORMATION: Val, Leu, Met, Ile, or His
<220> FEATURE:
<221> NAME/KEY: MOD_RES
<222> LOCATION: (51)
<223> OTHER INFORMATION: Gln, Arg, or Thr
<220> FEATURE:
<221> NAME/KEY: MOD_RES
<222> LOCATION: (52)
<223> OTHER INFORMATION: Thr, Ser, Ala, Asn, or His
<220> FEATURE:
<221> NAME/KEY: MOD_RES
<222> LOCATION: (53)
<223> OTHER INFORMATION: Leu, Asn, or Ile
<220> FEATURE:
<221> NAME/KEY: MOD_RES
<222> LOCATION: (54)
<223> OTHER INFORMATION: Val, Met, Leu, Pro, or Ile
<220> FEATURE:
<221> NAME/KEY: MOD_RES
<222> LOCATION: (55)
<223> OTHER INFORMATION: His, Asn, Arg, Lys, Tyr, or Gln
<220> FEATURE:
<221> NAME/KEY: MOD_RES
<222> LOCATION: (56)
<223> OTHER INFORMATION: Phe, Leu, Ser, Asn, Met, Ala, Arg, Glu, Gly,
      or Gln
<220> FEATURE:
<221> NAME/KEY: MOD_RES
<222> LOCATION: (57)
<223> OTHER INFORMATION: Ile, Met, Leu, Val, Lys, Gln, Ala, or Tyr
<220> FEATURE:
<221> NAME/KEY: MOD_RES
<222> LOCATION: (58)
<223> OTHER INFORMATION: Asn, Phe, Lys, Glu, Asp, Ala, Gln, Gly, Leu,
      or Val
<220> FEATURE:
<221> NAME/KEY: MOD_RES
<222> LOCATION: (59)
<223> OTHER INFORMATION: Pro, Asn, Ser, Val, or Asp
<220> FEATURE:
<221> NAME/KEY: MOD_RES
<222> LOCATION: (60)
<223> OTHER INFORMATION: Glu, Asp, Asn, Lys, Arg, Ser, Gly, Thr, Gln,
      Pro, or His
<220> FEATURE:
<221> NAME/KEY: MOD_RES
<222> LOCATION: (61)
<223> OTHER INFORMATION: Thr, His, Tyr, Ala, Ile, Lys, Asp, Ser, Gly,
      or Arg
<220> FEATURE:
<221> NAME/KEY: MOD_RES
<222> LOCATION: (62)
<223> OTHER INFORMATION: Val, Ile, Thr, Ala, Leu, or Ser
<220> FEATURE:
<221> NAME/KEY: MOD_RES
<222> LOCATION: (63)
<223> OTHER INFORMATION: Pro, Gly, Ser, Asp, or Ala
<220> FEATURE:
<221> NAME/KEY: MOD_RES
<222> LOCATION: (64)
<223> OTHER INFORMATION: Lys, Leu, Pro, Ala, Ser, Glu, Arg, or Gly
<220> FEATURE:
<221> NAME/KEY: MOD_RES
<222> LOCATION: (65)
<223> OTHER INFORMATION: Pro, Ala, Val, Thr, or Ser
<220> FEATURE:
<221> NAME/KEY: MOD_RES
<222> LOCATION: (66)
```

```
<223> OTHER INFORMATION: Cys, Val, or Ser
<220> FEATURE:
<221> NAME/KEY: MOD_RES
<222> LOCATION: (68)
<223> OTHER INFORMATION: Ala, Val, or Thr
<220> FEATURE:
<221> NAME/KEY: MOD_RES
<222> LOCATION: (70)
<223> OTHER INFORMATION: Thr, Ala, Glu, Val, Gly, Asp, or Tyr
<220> FEATURE:
<221> NAME/KEY: MOD_RES
<222> LOCATION: (71)
<223> OTHER INFORMATION: Gln, Lys, Glu, Arg, or Val
<220> FEATURE:
<221> NAME/KEY: MOD_RES
<222> LOCATION: (72)
<223> OTHER INFORMATION: Leu, Met, Thr, or Tyr
<220> FEATURE:
<221> NAME/KEY: MOD_RES
<222> LOCATION: (73)
<223> OTHER INFORMATION: Asn, Ser, Gly, Thr, Asp, Glu, Lys, or Val
<220> FEATURE:
<221> NAME/KEY: MOD_RES
<222> LOCATION: (74)
<223> OTHER INFORMATION: Ala, Pro, Gly, or Ser
<220> FEATURE:
<221> NAME/KEY: MOD_RES
<222> LOCATION: (75)
<223> OTHER INFORMATION: Ile, Thr, Leu, or Val
<220> FEATURE:
<221> NAME/KEY: MOD_RES
<222> LOCATION: (76)
<223> OTHER INFORMATION: Ser, Pro, Ala, Thr, Asn, or Gly
<220> FEATURE:
<221> NAME/KEY: MOD_RES
<222> LOCATION: (77)
<223> OTHER INFORMATION: Val, Ile, Leu, or Met
<220> FEATURE:
<221> NAME/KEY: MOD_RES
<222> LOCATION: (79)
<223> OTHER INFORMATION: Tyr, Phe, Arg, Thr, Tyr, or Met
<220> FEATURE:
<221> NAME/KEY: MOD_RES
<222> LOCATION: (80)
<223> OTHER INFORMATION: Phe, Tyr, His, Leu, Ile, Lys, Gln, or Val
<220> FEATURE:
<221> NAME/KEY: MOD_RES
<222> LOCATION: (81)
<223> OTHER INFORMATION: Asp, Leu, Asn, or Glu
<220> FEATURE:
<221> NAME/KEY: MOD_RES
<222> LOCATION: (82)
<223> OTHER INFORMATION: Asp, Ser, Arg, Asn, Glu, Ala, Lys, Gly, or Pro
<220> FEATURE:
<221> NAME/KEY: MOD_RES
<222> LOCATION: (83)
<223> OTHER INFORMATION: Ser, Asn, Asp, Tyr, Ala, Gly, Gln, Met, Glu,
      Asn, or Lys
<220> FEATURE:
<221> NAME/KEY: MOD_RES
<222> LOCATION: (84)
<223> OTHER INFORMATION: Ser, Asn, Glu, Asp, Val, Lys, Gly, Gln, or Arg
<220> FEATURE:
<221> NAME/KEY: MOD_RES
<222> LOCATION: (85)
<223> OTHER INFORMATION: Asn, Lys, Thr, Pro, Val, Ile, Arg, Ser, or Gln
<220> FEATURE:
<221> NAME/KEY: MOD_RES
<222> LOCATION: (86)
<223> OTHER INFORMATION: Val, Ile, Thr, or Ala
<220> FEATURE:
<221> NAME/KEY: MOD_RES
<222> LOCATION: (87)
<223> OTHER INFORMATION: Ile, Asn, Val, Leu, Tyr, Asp, or Ala
<220> FEATURE:
<221> NAME/KEY: MOD_RES
<222> LOCATION: (88)
<223> OTHER INFORMATION: Leu, Tyr, Lys, or Ile
<220> FEATURE:
```

```
<221> NAME/KEY: MOD_RES
<222> LOCATION: (89)
<223> OTHER INFORMATION: Lys, Arg, Asn, Tyr, Phe, Thr, Glu, or Gly
<220> FEATURE:
<221> NAME/KEY: MOD_RES
<222> LOCATION: (90)
<223> OTHER INFORMATION: Lys, Arg, His, Gln, Asn, Glu, or Val
<220> FEATURE:
<221> NAME/KEY: MOD_RES
<222> LOCATION: (91)
<223> OTHER INFORMATION: Tyr, His, Glu, or Ile
<220> FEATURE:
<221> NAME/KEY: MOD_RES
<222> LOCATION: (92)
<223> OTHER INFORMATION: Arg, Glu, Gln, Pro, or Lys
<220> FEATURE:
<221> NAME/KEY: MOD_RES
<222> LOCATION: (93)
<223> OTHER INFORMATION: Asn, Asp, Ala, Glu, Gly, or Lys
<220> FEATURE:
<221> NAME/KEY: MOD_RES
<222> LOCATION: (94)
<223> OTHER INFORMATION: Met or Ala
<220> FEATURE:
<221> NAME/KEY: MOD_RES
<222> LOCATION: (95)
<223> OTHER INFORMATION: Val, Ile, Ala, Thr, Ser, or Lys
<220> FEATURE:
<221> NAME/KEY: MOD_RES
<222> LOCATION: (96)
<223> OTHER INFORMATION: Val or Ala
<220> FEATURE:
<221> NAME/KEY: MOD_RES
<222> LOCATION: (97)
<223> OTHER INFORMATION: Arg, Lys, Gln, Asp, Glu, Val, Ala, Ser, or Thr
<220> FEATURE:
<221> NAME/KEY: MOD_RES
<222> LOCATION: (98)
<223> OTHER INFORMATION: Ala, Ser, Glu, Gly, Arg, or Thr
<220> FEATURE:
<221> NAME/KEY: MOD_RES
<222> LOCATION: (100)
<223> OTHER INFORMATION: Gly, Ala, or Thr
<220> FEATURE:
<221> NAME/KEY: MOD_RES
<222> LOCATION: (102)
<223> OTHER INFORMATION: His, Arg, Gly, Leu, or Ser

<400> SEQUENCE: 7

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Pro Xaa Xaa Xaa Xaa Xaa Xaa Cys Xaa Gly
            20                  25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Cys Xaa Pro Xaa Xaa Xaa Xaa Xaa Xaa Xaa Leu Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Cys Xaa Cys Xaa
            100

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      N-terminal sequence
```

```
<220> FEATURE:
<221> NAME/KEY: MOD_RES
<222> LOCATION: (2)
<223> OTHER INFORMATION: Lys, Arg, Ala, or Gln
<220> FEATURE:
<221> NAME/KEY: MOD_RES
<222> LOCATION: (3)
<223> OTHER INFORMATION: Lys, Arg, or Met
<220> FEATURE:
<221> NAME/KEY: MOD_RES
<222> LOCATION: (4)
<223> OTHER INFORMATION: His, Arg, or Gln
<220> FEATURE:
<221> NAME/KEY: MOD_RES
<222> LOCATION: (5)
<223> OTHER INFORMATION: Glu, Ser, His, Gly, Arg, Pro, Thr, or Tyr

<400> SEQUENCE: 8

Cys Xaa Xaa Xaa Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      N-terminal sequence
<220> FEATURE:
<221> NAME/KEY: MOD_RES
<222> LOCATION: (2)
<223> OTHER INFORMATION: Lys, Arg, Gln, Ser, His, Glu, Ala, or Cys
<220> FEATURE:
<221> NAME/KEY: MOD_RES
<222> LOCATION: (3)
<223> OTHER INFORMATION: Lys, Arg, Met, Lys, Thr, Leu, Tyr, or Ala
<220> FEATURE:
<221> NAME/KEY: MOD_RES
<222> LOCATION: (4)
<223> OTHER INFORMATION: His, Gln, Arg, Lys, Thr, Leu, Val, Pro, or Tyr
<220> FEATURE:
<221> NAME/KEY: MOD_RES
<222> LOCATION: (5)
<223> OTHER INFORMATION: Gln, Thr, His, Arg, Pro, Ser, Ala, Gln, Asn,
      Tyr, Lys, Asp, or Leu

<400> SEQUENCE: 9

Cys Xaa Xaa Xaa Xaa
1               5
```

METHOD FOR REPAIRING A DEFECT IN AN INTERVERTEBRAL DISC

This application is a continuation of U.S. application Ser. No. 11/192,542, filed Jul. 28, 2005, which is a divisional of U.S. application Ser. No. 09/828,607, filed Apr. 6, 2001, now U.S. Pat. No. 6,958,149, which is a continuation of PCT/US99/17222, filed Jul. 30, 1999, the entire disclosures of which are incorporated by reference herein.

FIELD OF THE INVENTION

This invention relates to the field of ligament and nonarticular cartilage tissue repair using osteogenic proteins.

BACKGROUND OF THE INVENTION

Osteogenic and chondrogenic proteins are able to induce the proliferation and differentiation of progenitor cells into functional bone, cartilage, tendon, and/or ligamentous tissue. These proteins, referred to herein as "osteogenic proteins," "morphogenic proteins" or "morphogens," include members of the bone morphogenetic protein ("BMP") family identified by their ability to induce endochondral bone morphogenesis. The osteogenic proteins generally are classified in the art as a subgroup of the TGF-β superfamily of growth factors. Hogan, *Genes & Development* 10:1580-1594 (1996). Osteogenic proteins include the mammalian osteogenic protein-1 (OP-1, also known as BMP-7) and its *Drosophila* homolog 60A, osteogenic protein-2 (OP-2, also known as BMP-8), osteogenic protein-3 (OP-3), BMP-2 (also known as BMP-2A or CBMP-2A) and its *Drosophila* homolog DPP, BMP-3, BMP-4 (also known as BMP-2B or CBMP-2B), BMP-5, BMP-6 and its murine homolog Vgr-1, BMP-9, BMP-10, BMP-11, BMP-12, BMP-13, BMP-14, BMP-15, GDF-5 (also known as CDMP-1 or MP52), GDF-6 (also known as CDMP-2), GDF-7 (also known as CDMP-3), the *Xenopus* homolog Vg1 and NODAL, UNIVIN, SCREW, ADMP, and NEURAL.

Osteogenic proteins typically include secretory peptides sharing common structural features. Processed from a precursor "pro-form," the mature form of an osteogenic protein is a disulfided-bonded homo- or hetero-dimer, with each subunit having a carboxyl terminal active domain. This domain has approximately 97-106 amino acid residues and contains a conserved pattern of cysteine residues. See, e.g., Massague, *Annu. Rev. Cell Biol.* 6:597 (1990); Sampath et al., *J. Biol. Chem.* 265:13198 (1990).

Osteogenic proteins can stimulate the proliferation and differentiation of progenitor cells when administered with an appropriate matrix or substrate to a mammal. As a result, they can induce bone formation, including endochondral bone formation, under conditions where true replacement bone would not otherwise occur. For example, when combined with a matrix material, osteogenic proteins induce formation of new bone in large segmental bone defects, spinal fusions, and fractures.

The larynx extends from the tongue to the trachea. The trachea is a cartilaginous and membranous tube extending from the lower end of the larynx to its division into the two principal bronchi. Fibrocartilaginous tissue is found in the larynx. Cartilage forms the skeletal framework of the larynx and is interconnected by ligaments and fibrous membranes. The hyoid bone is intimately associated with the larynx, although it is usually regarded as a separate structure with a distinct function.

Abnormalities of the laryngeal skeleton influence its respiratory, defensive and phonatory functions, and can result in suffocation or loss of voice. Abnormalities can be congenital, such as cleft larynx, or acquired, such as an edema of the glottis. Excessive ossification of one or more hyaline cartilage tissues also may limit the respiratory or phonatory function. Still other abnormalities include ulceration of the larynx as a result of disease, e.g., syphilis, tuberculosis or malignancy. Abnormalities also can result from mechanical trauma to the larynx or trachea, including complications from tracheotomies. Several diseases of the human larynx, including laryngeal cancer, involve the laryngeal skeleton. Treatment of these and other conditions may involve partial or complete removal of the laryngeal skeleton or trachea (tracheotomy, laryngotomy, or laryngotracheotomy). Surgical reconstructive procedures of the larynx or trachea are complex. To date, reconstruction has relied on cartilage grafts, small intestine grafts, and cellular adhesives such as fibrinogen or cyanoacrylate to reattach torn tissue. Common complications include graft rejection and/or fibrous transformation of autografts or allografts.

Fibrocartilaginous tissue is found not only in the larynx, but also in other regions including the ear, nose, ribs, intervertebral discs and interarticular menisci. Repair and reconstruction of defects in these tissues requires regeneration of appropriate functional replacement fibrocartilage.

SUMMARY OF THE INVENTION

The present invention provides methods and devices for inducing in vivo formation of functional (e.g., mechanically acceptable) replacement nonarticular cartilage and ligament tissues.

In a method of the invention, an osteogenic protein is provided in a biocompatible, bioresorbable carrier to a defect locus in a nonarticular cartilage tissue of a mammal, thereby inducing the formation of functional replacement cartilage tissue. The defect locus can be in the larynx, trachea, intervertebral discs, interarticular menisci, ear, nose, ribs, or other fibrocartilaginous tissues of the mammal. For instance, the method can be used to repair defects in cricoid, thyroid, arytenoid, cuneiform, corniculate and epiglottic cartilage tissues, as well as any other nonarticular hyaline cartilage tissues. Under certain circumstances, the osteogenic protein and the carrier are preferably placed under the perichondrium of the target tissue.

The carrier used in this invention is biocompatibic in that it is not toxic and does not elicit severe inflammatory reactions in the body. The carrier is also bioresorbable in that it can be at least partially, and preferably entirely, resorbed at the repaired locus within a clinically accentable period of time. e.g., 4 months to a year. The carrier can include a matrix or "scaffold" structure, or it can be substantially matrix-free. The carrier may be solid (e.g., porous or particulate), or in a gel, paste, liquid or other injectable form. Suitable carriers contain materials that include, but are not limited to, allogenic tissue (e.g., devitalized allogenic, autologous, or xenogenic cartilage tissue), collagen (e.g., Types I and II collagen), celluloses (e.g., alkylcelluloses such as carboxymethycellulose), calcium phosphates (e.g., hydroxyapatite)., poloxamers (e.g., PLURONIC F127®), gelatins, polyethylene glycols (e.g. PEG 3350), dextrins, vegetable oils (e.g., sesame oil), and polymers comprised of lactic acid, butyric acid, and/or glycolic acid. Autologous or autogenic blood can also be included in the carrier, because it has been found that such inclusion speeds up the healing process.

Also embraced within this invention are implantable devices for repairing nonarticular cartilage tissues or ligament tissues. Such devices contain one or more osteogenic proteins disposed in a carrier containing, e.g., devitalized cartilage, Type I collagen, or carboxymethylcellulose.

This invention also provides a method of promoting chondrogenesis at a defect locus in a mammal. In this method, an osteogenic protein is provided to a devitalized cartilage carrier to the defect locus, wherein the cartilage has been configured to fit into the defect locus.

Osteogenic proteins useful in this invention include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-β. As used herein, the terms "morphogen," "bone morphogen," "BMP," "osteogenic protein" and "osteogenic factor" embrace the class of proteins typified by human osteogenic protein 1 (hOP-1).

One of the preferred osteogenic proteins is OP-1. Nucleotide and amino acid sequences for hOP-1 are provided in SEQ ID NOs:1 and 2, respectively. For ease of description, hOP-1 is recited as a representative osteogenic protein. It will be appreciated by the ordinarily-skilled artisan, however, that OP-1 is merely representative of a family of morphogens.

This family of morphogens include biologically active variants of any of the above-listed proteins, including variants containing conservative amino acid changes; and osteogenically active proteins having the conserved seven-cysteine skeleton or domain as defined below. For instance, useful osteogenic proteins also include those containing sequences that share at least 70% amino acid sequence homology with the C-terminal seven-cysteine domain of hOP-1, which domain corresponds to the C-terminal 102-106 amino acid residues of SEQ ID NO:2.

To determine the percent homology of a candidate amino acid sequence to that seven-cysteine domain, the candidate sequence and the sequence of the domain are aligned. The alignment can be made with, e.g., the dynamic programming algorithm described in Needleman et al., *J. Mol. Biol.* 48:443 (1970), and the Align Program, a commercial software package produced by DNAstar, Inc.

The teachings by both sources are incorporated by reference herein. An initial alignment can be refined by comparison to a multi-sequence alignment of a family of related proteins. Once the alignment between the candidate sequence and the seven-cysteine domain is made and refined, a percent homology score is calculated.

The aligned amino acid residues of the two sequences are compared sequentially for their similarity to each other. Similarity factors include similar size, shape and electrical charge. One particularly preferred method of determining amino acid similarities is the PAM250 matrix described in Dayhoff et al., *Atlas of Protein Sequence and Structure* 5:345-352 (1978 & Supp.), herein incorporated by reference. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate sequence and the seven-cysteine domain. The geometric mean is the square root of the product of these scores. The normalized raw score is the percent homology.

Useful osteogenic proteins also include those containing sequences that share greater than 60% identity with the seven-cysteine domain. In other embodiments, useful osteogenic proteins are defined as osteogenically active proteins having any one of the generic sequences defined herein, including OPX (SEQ ID NO:3) and Generic Sequences 7 and 8 (SEQ ID NO:4 and SEQ ID NO:5, respectively), or Generic Sequences 9 and 10 (SEQ ID NO:6 and SEQ ID NO:7, respectively).

In another aspect, the instant invention provides a kit for practice of the above-described methods. As contemplated herein, one embodiment of a kit for inducing local laryngeal or tracheal tissue formation includes an improved device wherein the osteogenic protein and carrier are packaged in the same receptacle. In other embodiments, wetting or binding agent(s) also are provided and packaged separately from other components.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting.

DETAILED DESCRIPTION OF THE INVENTION

This invention is based on the discovery that osteogenic proteins can generate functional replacement nonarticular cartilage and/or ligament tissues when provided locally at a defect site in a mammal. Such nonarticular cartilage tissues include laryngeal, tracheal, and other fibrocartilaginous tissues such as the tissues of intervertebral discs, ribs, skeletal interarticular menisci, the ear and the nose. Devices, kits and methods of the invention are useful in restoring lost or impaired functions resulting from loss or injuries of these tissues in a mammal, e.g., a human.

In order for the invention to be more fully understood, various types of cartilage, cartilaginous tissues and organs are described below. Articular cartilage covers the articulating surfaces of the portions of bones in joints. The cartilage allows movement in joints without direct bone-to-bone contact, thereby preventing wearing down and damage of opposing bone surfaces. Articular cartilage has no tendency to ossification. The cartilage surface appears smooth and pearly macroscopically, and is finely granular under high power magnification. Such cartilage is referred to as hyaline cartilage, as opposed to fibrocartilage and elastic cartilage. Articular cartilage appears to derive its nutriment partly from the vessels of the neighboring synovial membrane, partly from those of the bone that it covers. Articular cartilage is associated with the presence of Type II and Type IX collagen and various well-characterized proteoglycans, and with the absence of Type X collagen, which is associated with endochondral bone formation. For a detailed description of articular cartilage micro-structure, see, for example, Aydelotte and Kuettner, *Conn. Tiss. Res.* 18:205 (1988); Zanetti et al., *J. Cell Biol.* 101:53 (1985); and Poole et al., *J. Anat.* 138:13 (1984).

Other types of permanent cartilage in adult mammals include fibrocartilage and elastic cartilage. In fibrocartilage, the mucopolysaccharide network is interlaced with prominent collagen bundles and the chondrocytes are more widely scattered than in hyaline cartilage. White fibrocartilage consists of a mixture of white fibrous tissue and cartilaginous tissue in various proportions. Secondary cartilaginous joints are formed by discs of fibrocartilage that join vertebrae in the vertebral column. Interarticular fibrocartilages are found in those joints which are most exposed to violent concussion and subject to frequent movement, e.g., the meniscus of the knee. Examples of such joints include the temporo-mandibular, sterno-clavicular, acromio-clavicular, wrist- and knee-joints. Such fibrocartilaginous discs, which adhere closely to both of the opposed surfaces, are composed of concentric rings of fibrous tissue, with cartilaginous laminae interposed. An example of such fibrocartilaginous discs is the intervertebral discs of the spine. Connecting fibrocartilages are interposed between the bony surfaces of those joints which admit of only slight mobility, as between the bodies of the vertebrae and between the pubic bones. Circumferential fibrocartilages surround the margin of some of the articular cavities, as the cotyloid cavity of the hip and the glenoid cavity of the shoulder; they serve to deepen the articular surface, and to protect its edges. Stratiform fibrocartilages refer to the thin coating to osseous grooves through which the tendons of certain muscles glide. Interarticular fibrocartilage is considered herein as nonarticular cartilage, so as to distinguish from articular cartilage that consists mainly of hyaline. When present in lesser amounts, as in articular discs, glenoid and acetabular labra, the cartilaginous lining of bony grooves for tendons and some articular cartilage, fibrocartilage is unlike other types of cartilage in having much Type I (general connective tissue) collagen in its matrix; it is then perhaps best regarded as a mingling of the two types of tissue, for example where a ligament or tendinous tissue inserts into hyaline cartilage, rather than a specific type of cartilage. See, e.g., Gray's Anatomy.

Elastic cartilage contains collagen fibers that are histologically similar to elastin fibers. Such cartilage is found in the human body in the auricle of the external ear, the Eustachian tubes, the cornicula laryngis, and the epiglottis. As with all cartilage, elastic cartilage also contains chondrocytes and a matrix, the latter being pervaded in every direction, by a network of yellow elastic fibers, branching and anastomosing in all directions except immediately around each cell, where there is a variable amount of non-fibrillated hyaline, intercellular substance.

As used herein "cartilage" is distinct from the fibrotic cartilaginous tissues, which occur in scar tissue, for example, and are keloid and typical of scar-type tissue, i.e., composed of capillaries and abundant, irregular, disorganized bundles of Type I and Type II collagen.

The primary laryngeal cartilages are either hyaline cartilage or fibrocartilage, particularly elastic fibrocartilage. Specifically, the corniculate, cuneiform, tritiate and epiglottic cartilages are elastic fibrocartilage with little tendency to ossify or calcify over time. The thyroid, cricoid and most of the arytenoid cartilage are hyaline cartilage and can undergo mottled calcification or ossification with age and can impair the mechanical acceptability of the tissue. The primary laryngeal ligaments include the extrinsic ligaments (e.g., thyrohoid membrane and its component ligaments), the intrinsic ligaments (e.g., cricothyroid membrane and its component ligaments), the vestibular folds and associated ligaments, the vocal folds and associated ligaments.

The trachea, or windpipe, is a cartilaginous and membranous cylindrical tube, flattened posteriorly. It extends from the lower part of the larynx, on a level with the sixth cervical vertebra, to opposite the fourth, or sometimes the fifth, dorsal vertebra, where it divides into two bronchi, one for each lung. The trachea is composed of imperfect, hyaline cartilaginous rings, which are completed by fibrous membrane. They are highly elastic, but sometimes become calcified in advanced life. The cartilages are enclosed in an elastic fibrous membrane.

I. Protein Considerations

In its mature, native form, a naturally occurring osteogenic protein is a glycosylated dimer, typically having an apparent molecular weight of about 30-36 kD as determined by SDS-PAGE. When reduced, the 30 kD protein gives rise to two glycosylated polypeptide subunits having apparent molecular weights of about 16 kD and 18 kD. In the reduced state, the protein has no detectable osteogenic activity. The unglycosylated protein, which also has osteogenic activity, has an apparent molecular weight of about 27 kD. When reduced, the 27 kD protein gives rise to two unglycosylated polypeptides, each having a molecular weight of about 14 kD to about 16 kD. Typically, naturally occurring osteogenic proteins are translated as a precursor having a N-terminal signal peptide usually less than about 30 amino acids in length. The signal peptide is followed by a "pro" domain that is cleaved to yield the mature C-terminal domain. The signal peptide is cleaved rapidly upon translation, at a cleavage site that can be predicted in a given sequence using the method of Von Heijne, *Nucleic Acids Research* 14:4683-4691 (1986). The pro domain usually is about three times larger than the fully processed mature C-terminal domain.

Osteogenic proteins useful herein include any known naturally occurring native proteins, including allelic, phylogenetic counterparts and other variants thereof. Useful osteogenic proteins also include those that are biosynthetically produced (e.g., including "muteins" or "mutant proteins") and those that are new, osteogenically active members of the general morphogenic family of proteins. Particularly useful sequences include those comprising the C-terminal 96 to 102 amino acid residues of: DPP (from *Drosophila*), Vg-1 (from *Xenopus*), Vgr-1 (from mouse), the OP1 and OP2 proteins (U.S. Pat. No. 5,011,691 and Oppermann et al.), as well as the proteins referred to as BMP-2, BMP-3, BMP-4 (WO 88/00205, U. S. Pat. No. 5,013,649 and WO 91/18098), BMP-5 and BMP-6 (WO 90/11366, PCT/U.S. 90/01630), BMP-8 and BMP-9. Other proteins useful in the practice of the invention include active forms of OP1, OP2, OP3, BMP-2, BMP-3, BMP-4, BMP-5, BMP-6, BMP-9, BMP-10, BMP-11, BMP-12, BMP-13, BMP-14, BMP-15, DPP, Vg-1, Vgr-1, 60A protein, GDF-1, GDF-3, GDF-5, GDF-6, GDF-7, GDF-8, GDF-9, and GDF-10, GDF-11, GDF-12, GDF-13, CDMP-3, UNIVIN, NODAL, SCREW, ADMP and NEURAL, and amino acid sequence variants thereof. In one currently preferred embodiment, useful osteogenic proteins include any one of OP-1, OP-2, OP-3, BMP-2, BMP-4, BMP-5, BMP-6, BMP-9, and amino acid sequence variants and homologs thereof, including species homologs thereof.

In certain preferred embodiments, useful osteogenic proteins include those having an amino acid sequence sharing at least 70% (e.g., at least 80%) sequence homology or "similarity" with all or part of a naturally occurring reference morphogenic protein. A preferred reference protein is human OP-1, and the reference sequence thereof is the C-terminal seven-cysteine domain present in osteogenically active forms of human OP-1. This domain corresponds to residues 330-431 of SEQ ID NO:2. Other known osteogenic proteins can also be used as a reference sequence. In one embodiment, a candidate amino acid sequence can be aligned with a reference amino acid sequence by using the method of Needleman et al., *J. Mol. Biol.* 48:443-453 (1970), implemented conveniently by computer programs such as the Align program (DNAstar, Inc.). Internal gaps and amino acid insertions in the candidate sequence are ignored for purposes of calculating the level of homology or identity between the candidate and reference sequences.

"Amino acid sequence homology" is understood herein to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. Certain particularly preferred morphogenic polypeptides share at least 60% (e.g., at least 65%) amino acid sequence identity with the C-terminal seven-cysteine domain of human OP-1.

As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al. (1978), 5 *Atlas of Protein Sequence and Structure, Suppl.* 3, Ch. 22, pp. 354-352, Natl. Biomed. Res. Found., Washington, D.C. 20007. Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative variant" or "conservative variation" also includes the use of a substituting amino acid residue in place of an amino acid residue in a given parent amino acid sequence, where antibodies specific for the parent sequence are also specific for, i.e., "cross-react" or "immuno-react" with, the resulting substituted polypeptide sequence.

In other preferred embodiments, the family of osteogenic proteins useful in the present invention are defined by a generic amino acid sequence. For example, Generic Sequence 7 (SEQ ID NO:4) and Generic Sequence 8 (SEQ ID NO:5), disclosed below, accommodate the homologies shared among preferred protein family members identified to date, including OP-1, OP-2, OP-3, BMP-2, BMP-3, BMP-4, BMP-5, BMP-6, 60A, DPP, Vg-1, Vgr-1, and GDF-1. The amino acid sequences for these proteins are described herein and/or in the art. The generic sequences include the identical amino acid residues shared by these sequences in the C-terminal six- or seven-cysteine skeletal domains (represented by Generic Sequences 7 and 8, respectively), as well as alternative residues for the variable positions within the sequences. The generic sequences provide an appropriate cysteine skeleton where inter- or intra-molecular disulfide bonds can form. Those sequences contain certain specified amino acids that may influence the tertiary structure of the folded proteins. In addition, the generic sequences allow for an additional cysteine at position 36 (Generic Sequence 7) or position 41 (Generic Sequence 8), thereby encompassing the biologically active sequences of OP-2 and OP-3.

GENERIC SEQUENCE 7

(SEQ ID NO: 4)
Leu Xaa Xaa Xaa Phe Xaa Xaa Xaa Gly Trp Xaa Xaa
 1               5                    10

-continued

GENERIC SEQUENCE 7

Xaa Xaa Xaa Xaa Pro Xaa Xaa Xaa Xaa Ala Xaa Tyr
            15                  20

Cys Xaa Gly Xaa Cys Xaa Xaa Pro Xaa Xaa Xaa Xaa
25                  30                      35

Xaa Xaa Xaa Xaa Asn His Ala Xaa Xaa Xaa Xaa Xaa
            40                      45

Xaa Xaa Xaa Xaa Xaa Xaa Xaa Xaa Xaa Xaa Xaa Xaa
    50                  55                  60

Cys Cys Xaa Pro Xaa Xaa Xaa Xaa Xaa Xaa Xaa Xaa
            65                  70

Leu Xaa Xaa Xaa Xaa Xaa Xaa Xaa Val Xaa Leu Xaa
            75                  80

Xaa Xaa Xaa Xaa Met Xaa Val Xaa Xaa Cys Xaa Cys
 85              90                      95

Xaa wherein each Xaa is independently defined as follows ("Res." means "residue"): Xaa at res.2=(Tyr or Lys); Xaa at res.3= (Val or Ile); Xaa at res.4=(Ser, Asp or Glu); Xaa at res.6=(Arg, Gln, Ser, Lys or Ala); Xaa at res.7=(Asp or Glu); Xaa at res.8=(Leu, Val or Ile); Xaa at res.11=(Gln, Leu, Asp, His, Asn or Ser); Xaa at res.12=(Asp, Arg, Asn or Glu); Xaa at res.13=(Trp or Ser); Xaa at res.14=(Ile or Val); Xaa at res.15= (Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln, Ala or Ser); Xaa at res.28= (Glu, Lys, Asp, Gln or Ala); Xaa at res.30=(Ala, Ser, Pro, Gln, Ile or Asn); Xaa at res.31=(Phe, Leu or Tyr); Xaa at res.33= (Leu, Val or Met); Xaa at res.34=(Asn, Asp, Ala, Thr or Pro); Xaa at res.35=(Ser, Asp, Glu, Leu, Ala or Lys); Xaa at res.36= (Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu, Met or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val, Gly or Leu); Xaa at res.53=(Asn, Lys, Ala, Glu, Gly or Phe); Xaa at res.54=(Pro, Ser or Val); Xaa at res.55=(Glu, Asp, Asn, Gly, Val, Pro or Lys); Xaa at res.56=(Thr, Ala, Val, Lys, Asp, Tyr, Ser, Gly, Ile or His); Xaa at res.57=(Val, Ala or Ile); Xaa at res.58=(Pro or Asp); Xaa at res.59=(Lys, Leu or Glu); Xaa at res.60=(Pro, Val or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=Ala, Pro or Ser); Xaa at res.70=(Ile, Thr, Val or Leu); Xaa at res.71=(Ser, Ala or Pro); Xaa at res.72=(Val, Leu, Met or Ile); Xaa at res.74=(Tyr or Phe); Xaa at res.75=(Phe, Tyr, Leu or His); Xaa at res.76= (Asp, Asn or Leu); Xaa at res.77=(Asp, Glu, Asn, Arg or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His, Arg or Val); Xaa at res.86=(Tyr, Glu or His); Xaa at res.87=(Arg, Gln, Glu or Pro); Xaa at res.88=(Asn, Glu, Trp or Asp); Xaa at res.90=(Val, Thr, Ala or Ile); Xaa at res.92=(Arg, Lys, Val, Asp, Gln or Glu); Xaa at res.93=(Ala, Gly, Glu or Ser); Xaa at res.95=(Gly or Ala); and Xaa at res.97=(His or Arg).

Generic Sequence 8 (SEQ ID NO:5) includes all of Generic Sequence 7 and in addition includes the following five amino acid at its N-terminus: Cys Xaa Xaa Xaa Xaa (SEQ ID NO:8), wherein Xaa at res.2=(Lys, Arg, Ala or Gln); Xaa at res.3=(Lys, Arg or Met); Xaa at res.4=(His, Arg or Gln); and Xaa at res.5=(Glu, Ser, His, Gly, Arg, Pro, Thr, or Tyr). Accordingly, beginning with residue 7, each "Xaa" in Generic Sequence 8 is a specified amino acid as defined as for Generic Sequence 7, with the distinction that each residue number described for Generic Sequence 7 is shifted by five in Generic Sequence 8. For example, "Xaa at res.2=(Tyr or Lys)" in Generic Sequence 7 corresponds to Xaa at res.7 in Generic Sequence 8.

In another embodiment, useful osteogenic proteins include those comprising sequences defined by Generic Sequences 9 (SEQ ID NO:6) and 10 (SEQ ID NO:7). Generic Sequences 9 and 10 are composite amino acid sequences of the following proteins: human OP-1, human OP-2, human OP-3, human BMP-2, human BMP-3, human BMP-4, human BMP-5, human BMP-6, human BMP-9, human BMP10, human BMP-11, *Drosophila* 60A, *Xenopus* Vg-1, sea urchin UNIVIN, human CDMP-1 (mouse GDF-5), human CDMP-2 (mouse GDF-6, human BMP-13), human CDMP-3 (mouse GDF-7, human BMP-12), mouse GDF-3, human GDF-1, mouse GDF-1, chicken DORSALIN, DPP, Drosophila SCREW, mouse NODAL, mouse GDF-8, human GDF-8, mouse GDF-9, mouse GDF-10, human GDF-11, mouse GDF-11, human BMP-15, and rat BMP3b. Like Generic Sequence 7, Generic Sequence 9 accommodates the C-terminal six-cysteine skeleton and, like Generic Sequence 8, Generic Sequence 10 accommodates the C-terminal seven-cysteine skeleton.

---

GENERIC SEQUENCE 9

(SEQ ID NO: 6)

```
Xaa Xaa Xaa Xaa Xaa Xaa Xaa Xaa Xaa Xaa Xaa Xaa
1               5                   10

Xaa Xaa Xaa Xaa Pro Xaa Xaa Xaa Xaa Xaa Xaa Xaa
            15                  20

Cys Xaa Gly Xaa Cys Xaa Xaa Xaa Xaa Xaa Xaa
25              30                      35

Xaa Xaa Xaa Xaa Xaa Xaa Xaa Xaa Xaa Xaa Xaa
                40                  45

Xaa Xaa Xaa Xaa Xaa Xaa Xaa Xaa Xaa Xaa Xaa
50          55                  60

Xaa Cys Xaa Pro Xaa Xaa Xaa Xaa Xaa Xaa Xaa
        65                          70

Leu Xaa Xaa Xaa Xaa Xaa Xaa Xaa Xaa Xaa Xaa
            75                  80

Xaa Xaa Xaa Xaa Xaa Xaa Xaa Xaa Cys Xaa Cys
85              90                      95

Xaa
```

--- wherein each Xaa is independently defined as follows: Xaa at res.1=(Phe, Leu or Glu); Xaa at res.2=(Tyr, Phe, His, Arg, Thr, Lys, Gln, Val or Glu); Xaa at res.3=(Val, Ile, Leu or Asp); Xaa at res.4=(Ser, Asp, Glu, Asn or Phe); Xaa at res.5=(Phe or Glu); Xaa at res.6=(Arg, Gln, Lys, Ser, Glu, Ala or Asn); Xaa at res.7=(Asp, Glu, Leu, Ala or Gln); Xaa at res.8=(Leu, Val, Met, Ile or Phe); Xaa at res.9=(Gly, His or Lys); Xaa at res.10=(Trp or Met); Xaa at res.11=(Gln, Leu, His, Glu, Asn, Asp, Ser or Gly); Xaa at res.12=(Asp, Asn, Ser, Lys, Arg, Glu or His); Xaa at res.13=(Trp or Ser); Xaa at res.14=(Ile or Val); Xaa at res.15=(Ile or Val); Xaa at res.16=(Ala, Ser, Tyr or Trp); Xaa at res.18=(Glu, Lys, Gln, Met, Pro, Leu, Arg, His or Lys); Xaa at res.19=(Gly, Glu, Asp, Lys, Ser, Gln, Arg or Phe); Xaa at res.20=(Tyr or Phe); Xaa at res.21=(Ala, Ser, Gly, Met, Gln, His, Glu, Asp, Leu, Asn, Lys or Thr); Xaa at res.22=(Ala or Pro); Xaa at res.23=(Tyr, Phe, Asn, Ala or Arg); Xaa at res.24=(Tyr, His, Glu, Phe or Arg); Xaa at res.26=(Glu, Asp, Ala, Ser, Tyr, His, Lys, Arg, Gln or Gly); Xaa at res.28=(Glu, Asp, Leu, Val, Lys, Gly, Thr, Ala or Gln); Xaa at res.30=(Ala, Ser, Ile, Asn, Pro, Glu, Asp, Phe, Gln or Leu); Xaa at res.31=(Phe, Tyr, Leu, Asn, Gly or Arg); Xaa at res.32=(Pro, Ser, Ala or Val); Xaa at res.33=(Leu, Met, Glu, Phe or Val); Xaa at res.34=(Asn, Asp, Thr, Gly, Ala, Arg, Leu or Pro); Xaa at res.35=(Ser, Ala, Glu, Asp, Thr, Leu, Lys, Gln or His); Xaa at res.36=(Tyr, His, Cys, Ile, Arg, Asp, Asn, Lys, Ser, Glu or Gly); Xaa at res.37=(Met, Leu, Phe, Val, Gly or Tyr); Xaa at res.38=(Asn, Glu, Thr, Pro, Lys, His, Gly, Met, Val or Arg); Xaa at res.39=(Ala, Ser, Gly, Pro or Phe); Xaa at res.40=(Thr, Ser, Leu, Pro, His or Met); Xaa at res.41=(Asn, Lys, Val, Thr or Gln); Xaa at res.42=(His, Tyr or Lys); Xaa at res.43=(Ala, Thr, Leu or Tyr); Xaa at res.44=(Ile, Thr, Val, Phe, Tyr, Met or Pro); Xaa at res.45=(Val, Leu, Met, Ile or His); Xaa at res.46=(Gln, Arg or Thr); Xaa at res.47=(Thr, Ser, Ala, Asn or His); Xaa at res.48=(Leu, Asn or Ile); Xaa at res.49=(Val, Met, Leu, Pro or Ile); Xaa at res.50=(His, Asn, Arg, Lys, Tyr or Gln); Xaa at res.51=(Phe, Leu, Ser, Asn, Met, Ala, Arg, Glu, Gly or Gln); Xaa at res.52=(Ile, Met, Leu, Val, Lys, Gln, Ala or Tyr); Xaa at res.53=(Asn, Phe, Lys, Glu, Asp, Ala, Gln, Gly, Leu or Val); Xaa at res.54=(Pro, Asn, Ser, Val or Asp); Xaa at res.55=(Glu, Asp, Asn, Lys, Arg, Ser, Gly, Thr, Gln, Pro or His); Xaa at res.56=(Thr, His, Tyr, Ala, Ile, Lys, Asp, Ser, Gly or Arg); Xaa at res.57=(Val, Ile, Thr, Ala, Leu or Ser); Xaa at res.58=(Pro, Gly, Ser, Asp or Ala); Xaa at res.59=(Lys, Leu, Pro, Ala, Ser, Glu, Arg or Gly); Xaa at res.60=(Pro, Ala, Val, Thr or Ser); Xaa at res.61=(Cys, Val or Ser); Xaa at res.63=(Ala, Val or Thr); Xaa at res.65=(Thr, Ala, Glu, Val, Gly, Asp or Tyr); Xaa at res.66=(Gln, Lys, Glu, Arg or Val); Xaa at res.67=(Leu, Met, Thr or Tyr); Xaa at res.68=(Asn, Ser, Gly, Thr, Asp, Glu, Lys or Val); Xaa at res.69=(Ala, Pro, Gly or Ser); Xaa at res.70=(Ile, Thr, Leu or Val); Xaa at res.71=(Ser, Pro, Ala, Thr, Asn or Gly); Xaa at res.72=(Val, Ile, Leu or Met); Xaa at res.74=(Tyr, Phe, Arg, Thr, Tyr or Met); Xaa at res.75=(Phe, Tyr, His, Leu, Ile, Lys, Gln or Val); Xaa at res.76=(Asp, Leu, Asn or Glu); Xaa at res.77=(Asp, Ser, Arg, Asn, Glu, Ala, Lys, Gly or Pro); Xaa at res.78=(Ser, Asn, Asp, Tyr, Ala, Gly, Gln, Met, Glu, Asn or Lys); Xaa at res.79=(Ser, Asn, Glu, Asp, Val, Lys, Gly, Gln or Arg); Xaa at res.80=(Asn, Lys, Thr, Pro, Val, Ile, Arg, Ser or Gln); Xaa at res.81=(Val, Ile, Thr or Ala); Xaa at res.82=(Ile, Asn, Val, Leu, Tyr, Asp or Ala); Xaa at res.83=(Leu, Tyr, Lys or Ile); Xaa at res.84=(Lys, Arg, Asn, Tyr, Phe, Thr, Glu or Gly); Xaa at res.85=(Lys, Arg, His, Gln, Asn, Glu or Val); Xaa at res.86=(Tyr, His, Glu or Ile); Xaa at res.87=(Arg, Glu, Gln, Pro or Lys); Xaa at res.88=(Asn, Asp, Ala, Glu, Gly or Lys); Xaa at res.89=(Met or Ala); Xaa at res.90=(Val, Ile, Ala, Thr, Ser or Lys); Xaa at res.91=(Val or Ala); Xaa at res.92=(Arg, Lys, Gln, Asp, Glu, Val, Ala, Ser or Thr); Xaa at res.93=(Ala, Ser, Glu, Gly, Arg or Thr); Xaa at res.95=(Gly, Ala or Thr); and Xaa at res.97=(His, Arg, Gly, Leu or Ser). Further, after res.53 in rat BMP3b and mouse GDF-10 there is an Ile; after res.54 in GDF-1 there is a Thr; after res.54 in BMP3 there is a Val; after res.78 in BMP-8 and DORSALIN there is a Gly; after res.37 in human GDF-1 there are Pro, Gly, Gly, and Pro.

Generic Sequence 10 (SEQ ID NO:7) includes all of Generic Sequence 9 and in addition includes the following five amino acid residues at its N-terminus: Cys Xaa Xaa Xaa Xaa (SEQ ID NO:9), wherein Xaa at res.2=(Lys, Arg, Gln, Ser, His, Glu, Ala, or Cys); Xaa at res.3=(Lys, Arg, Met, Lys, Thr, Leu, Tyr, or Ala); Xaa at res.4=(His, Gln, Arg, Lys, Thr, Leu, Val, Pro, or Tyr); and Xaa at res.5=(Gln, Thr, His, Arg, Pro, Ser, Ala, Gln, Asn, Tyr, Lys, Asp, or Leu). Accordingly, beginning at res.6, each "Xaa" in Generic Sequence 10 is a specified amino acid defined as for Generic Sequence 9, with the distinction that each residue number described for Generic Sequence 9 is shifted by five in Generic Sequence 10. For example, "Xaa at res.1=(Phe, Leu or Glu)" in Generic Sequence 9 corresponds to Xaa at res.6 in Generic Sequence 10.

As noted above, certain preferred bone morphogenic proteins useful in this invention have greater than 60%, preferably greater than 65%, identity with the C-terminal seven-cysteine domain of human OP-1. These particularly preferred sequences include allelic and phylogenetic variants of the OP-1 and OP-2 proteins, including the *Drosophila* 60A protein. Accordingly, in certain particularly preferred embodiments, useful proteins include active proteins comprising dimers having the generic amino acid sequence "OPX" (SEQ ID NO:3), which defines the seven-cysteine skeleton and accommodates the homologies between several identified variants of OP-1 and OP-2. Each Xaa in OPX is independently selected from the residues occurring at the corresponding position in the C-terminal sequence of mouse or human OP-1 or OP-2.

```
                              OPX
                                              (SEQ ID NO: 3)
Cys Xaa Xaa His Glu Leu Tyr Val Ser Phe Xaa Asp
1               5                   10

Leu Gly Trp Xaa Asp Trp Xaa Ile Ala Pro Xaa Gly
            15              20

Tyr Xaa Ala Tyr Tyr Cys Glu Gly Glu Cys Xaa Phe
25                  30                  35

Pro Leu Xaa Ser Xaa Met Asn Ala Thr Asn His Ala
            40              45

Ile Xaa Gln Xaa Leu Val His Xaa Xaa Xaa Pro Xaa
    50              55                      60

Xaa Val Pro Lys Xaa Cys Cys Ala Pro Thr Xaa Leu
                65                  70

Xaa Ala Xaa Ser Val Leu Tyr Xaa Asp Xaa Ser Xaa
    75                  80

Asn Val Ile Leu Xaa Lys Xaa Arg Asn Met Val Val
85              90                      95

Xaa Ala Cys Gly Cys His
            100
``` wherein Xaa at res.2=(Lys or Arg); Xaa at res.3=(Lys or Arg); Xaa at res.11=(Arg or Gln); Xaa at res.16=(Gln or Leu); Xaa at res.19=(Ile or Val); Xaa at res.23=(Glu or Gln); Xaa at res.26=(Ala or Ser); Xaa at res.35=(Ala or Ser); Xaa at res.39=(Asn or Asp); Xaa at res.41=(Tyr or Cys); Xaa at res.50=(Val or Leu); Xaa at res.52=(Ser or Thr); Xaa at res.56=(Phe or Leu); Xaa at res.57=(Ile or Met); Xaa at res.58=(Asn or Lys); Xaa at res.60=(Glu, Asp or Asn); Xaa at res.61=(Thr, Ala or Val); Xaa at res.65=(Pro or Ala); Xaa at res.71=(Gln or Lys); Xaa at res.73=(Asn or Ser); Xaa at res.75=(Ile or Thr); Xaa at res.80=(Phe or Tyr); Xaa at res.82=(Asp or Ser); Xaa at res.84=(Ser or Asn); Xaa at res.89=(Lys or Arg); Xaa at res.91=(Tyr or His); and Xaa at res.97=(Arg or Lys).

In still another preferred embodiment, useful osteogenically active proteins comprise an amino acid sequence encoded by a nucleic acid that hybridizes, under low, medium or high stringency hybridization conditions, to DNA or RNA encoding reference osteogenic sequences. Exemplary reference sequences include the C-terminal sequences defining the conserved seven-cysteine domains of OP-1, OP-2, BMP-2, BMP-4, BMP-5, BMP-6, 60A, GDF-3, GDF-5, GDF-6, GDF-7, and the like. High stringent hybridization conditions are herein defined as hybridization in 40% formamide, 5X SSPE, 5X Denhardt's Solution, and 0.1% SDS at 37° C. overnight, and washing in 0.1X SSPE, 0.1% SDS at 50° C. Standard stringency conditions are well characterized in commercially available, standard molecular cloning texts. See, for example, *Molecular Cloning A Laboratory Manual*, 2nd Ed., ed. by Sambrook et al. (Cold Spring Harbor Laboratory Press 1989); *DNA Cloning*, Volumes I and II (D. N. Glover ed., 1985); *Oligonucleotide Synthesis* (M. J. Gait ed., 1984); *Nucleic Acid Hybridization* (B. D. Hames & S. J. Higgins eds. 1984); and B. Perbal, *A Practical Guide To Molecular Cloning* (1984).

The osteogenic proteins contemplated herein can be expressed from intact or truncated genomic DNA or cDNA, or from synthetic DNAs, in prokaryotic or eukaryotic host cells. The dimeric proteins can be isolated from the culture media and/or refolded and dimerized in vitro to form biologically active compositions. Heterodimers can be formed in vitro by combining separate, distinct polypeptide chains. Alternatively, heterodimers can be formed in a single cell by co-expressing nucleic acids encoding separate, distinct polypeptide chains. See, e.g., WO 93/09229 and U.S. Pat. No. 5,411,941, for exemplary protocols for recombinant heterodimer protein production. Currently preferred host cells include, without limitation, prokaryotes including *E. coli*, and eukaryotes including yeast (e.g., *Saccharomyces*) or mammalian cells (e.g., CHO, COS or BSC cells). Other host cells can also be used to advantage. Detailed descriptions of the proteins useful in the practice of this invention, including how to make, use and test them for osteogenic activity, are disclosed in numerous publications, including U.S. Pat. Nos. 5,266,683 and 5,011,691, the disclosures of which are incorporated by reference herein.

II. Formulation and Delivery Considerations

A. General Considerations

Devices and compositions of the invention can be formulated using routine methods. Useful formulation methodologies include lyophilization of solubilized protein onto matrix or carrier materials. Useful protein solubilization solutions include ethanol, urea, physiological buffers (e.g., saline), acidic buffers, and acetonitrile/trifluoroacetic acid solutions, and the like. See, for example, U.S. Pat. No. 5,266,683. The desired final concentration of protein will depend on the specific activity of the protein as well as the type, volume, and anatomical location of the defect. In one preferred embodiment, useful proteins have half maximal bone forming specific activity of 0.5-1.0 ng protein/25 mg matrix. Proteins having lower specific activity may also be used. The desired final concentration of protein may depend on the age, sex and overall health of the recipient. For example, 10-1000 μg osteogenic protein per 4 cm² of defect is a generally effective dose. Smaller quantities may suffice for smaller defects or tears. Optimization of dosages requires no more than routine experimentation and is within the skill of the art.

A device of the invention can assume a variety of configurations. It can comprise a synthetic or natural-sourced matrix configured in size and shape to fit the defect site to be repaired. Alternatively, the device can comprise a carrier to formulate a gel, paste, putty, cement, sheet or liquid. For example, a matrix-free osteogenic device in solution can be formulated by solubilizing certain forms of OP-1 in acetate (20 mM, pH 4.5) or citrate buffers, or phosphate-buffered saline (pH 7.5). In some instances, the osteogenic protein may not be entirely solubilized and may precipitate upon administration into the defect locus. Suspensions, aggregate formation or in vivo precipitation does not impair the operativeness of the matrix-free osteogenic device when practiced in accordance with the invention disclosed herein. Matrix-free devices in liquid or semi-liquid forms are particularly suitable for administration by injection, so as to provide the device to a defect locus by injection rather than surgical means. A series of matrix-free devices is described below. Matrix materials, including particulate materials, also can be added to these devices, to advantage.

In yet another embodiment of the present invention, the osteogenic device is prepared immediately prior to its delivery to the defect locus. For example, carboxymethylcellulose (CMC) containing devices can be prepared on-site, suitable for admixing immediately prior to surgery. In one embodiment, low viscosity CMC (AQUALON®) is packaaed and irradiated separately from the osteogenic protein OP-1. The OP-1 protein then is admixed with the CMC carrier, and tested for osteogenic activity. Devices prepared in this manner are as biologically active as the conventional device without CMC. The devices repair defect loci by inducing cartilage or tissue formation. The amount of osteogenic protein effective for this purpose can be readily determined by one skilled in the art.

B. Preparations of Bone Morphogenic Proteins

The following illustrates methods for preparing lyophilized OP-1. Other lyophilized osteogenic proteins can be prepared in a similar manner.

OP-1 is lyophilized from 20 mM (pH 4.5) acetate buffer with 5% mannitol, lactose, glycine or other additive or bulking agent, using standard lyophilization protocols. OP-1 prepared in this manner can remain biologically active for at least six months when stored at 4° C. to 30° C.

OP-1 can also be lyophilized from a succinate or citrate buffer (or other non-volatile buffer) for re-constitution in water, or from water for re-constitution in 20 mM (pH 4.5) acetate buffer. Generally, additives such as lactose, sucrose, glycine and mannitol are suitable for use in lyophilized matrix-free osteogenic devices. In certain embodiments, such devices (0.5 mg/ml OP-1 and 5% additive) can be prepared in a wet or dry configuration prior to lyophilization.

For example, liquid formulations of OP-1 in 10 and 20 mM acetate buffer (pH 4, 4.5 and 5) with and without mannitol (0%, 1% and 5%) are stable and osteogenically active for at least six months.

III. Bioassays

An art-recognized bioassay for bone induction is described in Sampath et al., *Proc. Natl. Acad. Sci. USA* 80:6591-6595 (1983) and U.S. Pat. No. 4,968,590, incorporated by reference herein. The assay entails depositing test samples in subcutaneous sites in recipient rats under ether anesthesia. A 1 cm vertical incision is made under sterile conditions in the skin over the thoracic region, and a pocket is prepared by blunt dissection. In certain circumstances, approximately 25 mg of the test sample is implanted deep into the pocket and the incision is closed with a metallic skin clip. The heterotropic site allows for the study of bone induction without the possible ambiguities resulting from the use of orthotropic sites.

The sequential cellular reactions occurring at the heterotropic site are complex. The multi-step cascade of endochondral bone formation includes: binding of fibrin and fibronectin to implanted matrix, chemotaxis of cells, proliferation of fibroblasts, differentiation into chondroblasts, cartilage formation, vascular invasion, bone formation, remodeling, and bone marrow differentiation.

Successful implants exhibit a controlled progression through the various stages of induced endochondral bone development, which include: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoblastic and bone remodeling on days twelve to eighteen; and (8) hematopoietic bone marrow differentiation in the ossicle on day twenty-one.

Histological sectioning and staining is preferred to determine the extent of osteogenesis in the implants. Staining with toluidine blue or hemotoxylin/eosin clearly demonstrates the ultimate development of endochondral bone. A twelve-day bioassay is sufficient to determine whether bone inducing activity is associated with the test sample.

Additionally, alkaline phosphatase activity can be used as a marker for osteogenesis. The enzyme activity can be determined spectrophotometrically after homogenization of the excised test material. The activity peaks at 9-10 days in vivo and thereafter slowly declines. Samples showing no bone development by histology should have no alkaline phosphatase activity under these assay conditions. The assay is useful for quantifying bone formation shortly after the test samples are removed from the rat. For example, samples containing osteogenic protein at several levels of purity have been tested to determine the most effective dose/purity level, in order to seek a formulation that can be produced on an industrial scale. The results as measured by alkaline phosphatase activity level and histological evaluation can be represented as "bone forming units." One bone forming unit represents the amount of protein required for half maximal bone forming activity on day 12. Additionally, dose curves can be constructed for bone inducing activity in vivo at each step of a purification scheme by assaying the protein concentration obtained at the step. Construction of such curves require only routine experimentation.

IV. EXAMPLES

The following examples are meant to illustrate the methods and materials of the present invention. Suitable modifications and adaptations of the described conditions and parameters normally encountered in the art which are obvious to those skilled in the art are within the spirit and scope of this invention.

Example 1

This example demonstrates the efficacy of osteogenic protein in regenerating functional replacement laryngeal tissue in a canine (beagle) model.

To prepare an osteogenic device, donor canine thyroid lamina, which was to be used as an allograft matrix, was frozen and thawed several times to release and remove cells. The thyroid lamina was then demineralized in 0.5 N HCl (e.g., four exchanges of 10 volumes of solution; 2 hours per exchange). A 4.5 cm² piece of treated thyroid allograft matrix was coated with about 250 μg mature OP-1 to form an implantable osteogenic device.

Surgery was performed using standard procedures. A 2 cm² defect was created in the left lamina of the thyroid cartilage of the host animal after careful preparation of the perichondrium. The implant was adjusted to fit the defect and incorporated with several stitches. The perichondrium and adjacent muscles then were replaced. Following recovery, the animal was allowed unrestricted motion. The animal was sacrificed at 18 postoperative weeks.

Prior to sacrifice, the healing progress was monitored visually and by palpation. Surgery and recovery did not result in loss of voice. Manual manipulation identified no gross abnormality and suggested that pliant, mechanically acceptable tissue had formed. Following sacrifice, the entire larynx was dissected and fixed in 4% paraformaldehyde and post-fixed in 70% ethanol. Careful dissection of all soft tissues identified no ossification or pathological structures such as pathological mineralization, aberrant vascularization and the like. The thyroid cartilage was well shaped on both the operated and unoperated sides and it was difficult to indicate the operated side. The thyroid cartilage was of cartilage-like color with no appearance of increased vascularization. By palpation only a slight protrusion of about 2 mm could be found at the reconstructed side. Maximal finger pressure indicated no instability of the replacement cartilage. The new tissue was similar in strength, flexibility and pliability to the original tissue. No interference with laryngeal rays of motion was educed.

Histological analysis indicated good incorporation of the newly formed cartilage and bone into the defect area. The new cartilage tissue appeared to be permanent, i.e., stable, and not subject to resorption as evidenced by its continued existence at 4 months post-operation. Temporary cartilage typically is resorbed or converted to fibrotic tissue within 3 months. Osteoblasts and new bone formation were identified in portions of the tissue, indicating the occurrence of osteogenesis.

These data demonstrated that thyroid cartilage allograft pre-coated with OP-1 induced the formation of a mechanically acceptable reconstruction of a surgically created thyroid cartilage defect. A cartilaginous carrier was shown to be acceptable with no rapid release to adjacent structures. Thus, OP-1 can be used to stimulate cartilage growth and repair.

Example 2

This example provides a protocol for determining the efficacy of osteogenic protein in repairing large laryngeal tissue defects and for comparative measurement of alternative carriers and osteogenic protein concentrations.

Here, a range of protein concentrations, i.e., 100 μg-500 μg, and two different surgical protocols, i.e., devices implanted under perichondrium and devices implanted under fascia, are tested. It is contemplated that fascia provides fewer progenitor cells than perichondrium. Animals are sacrificed at 16 weeks. Table I below summarizes the protocol.

TABLE I

| | | | Experiment Protocol | |
|---|---|---|---|---|
| Group | Dogs | Defect | Implant | Duration |
| I | 3 | Partial (⅔ of the right side of the thyroid cartilage) | Control cartilage under the perichondrium | 4 months |
| II | 3 | Partial (⅔ of the right side of the thyroid cartilage) | 100 μg OP-1 + cartilage under the perichondrium | 4 months |
| III | 3 | Partial (⅔ of the right side of the thyroid cartilage) | 500 μg OP-1 + cartilage under the perichondrium | 4 months |
| IV | 3 | Partial (⅔ of the right side of the thyroid cartilage) | 500 μg OP-1 + cartilage under the fascia | 4 months |
| V | 3 | Partial (⅔ of the right side of the thyroid cartilage) | 500 μg OP-1 + GuHCl-extracted cartilage under the perichondrium | 4 months |

Example 3

This example provides a protocol for determining the efficacy of a synthetic matrix in repairing laryngeal tissue in a mammal.

Cleft defects are surgically created in ⅔ of one side of the thyroid cartilage in the test animal. The defect sizes range from 2.0-4.5 cm². To prepare an osteogenic device, one of the following three types of matrices/carriers is used: (i) bone collagen matrix that has been demineralized, gaudier-extracted, and combined with CMC, e.g., 0.15-0.25 g of CMC/g polymer, to maximize conciseness, integrity and handling properties; (ii) synthetic collagen-GAG matrix; and (iii) matrix-free carriers. The amount of osteogenic protein is (i) 50 μg/defect; (ii) 100 μg/defect; (iii) 500 μg/defect; or (iv) 750 μg/defect. The surgery protocol for implanting the osteogenic device involves replacement of perichondrium, or removal of perichondrium and replacement of fascia and muscles only.

Animals are treated as described in Example 1. Animals are sacrificed at 12 weeks, 18 weeks, 24 weeks and 36 weeks.

The mechanical integrity of the target tissue can be evaluated using standard protocols for measuring load-bearing capacity, range of motion, compressive strength, and the like.

It is anticipated that all matrix components will result in mechanically acceptable replacement tissue formation and that at 24 weeks or 36 weeks, histology will reveal stable cartilage formation.

Example 4

This example provides a protocol for determining the efficacy of osteogenic protein in regenerating mechanically acceptable, functional replacement larynx following partial or complete laryngoctomy.

Here, a defect sufficient to remove at least ⅔ of the larynx and involving multiple laryngeal ligaments and cartilages is created. A replacement allograft matrix is created, using, for example, the protocol described in Example 1 or 2, or the protocol described in PCT publication WO 95/33502.

The replacement matrix is coated with osteogenic protein as described above (e.g., 10-1000 μg OP-1) and surgically implanted. Animals are monitored visually and by manual manipulation, and sacrificed at 12 weeks, 18 weeks, 24 weeks and 36 weeks post-operation. It is anticipated that full incorporation of the graft will result in the formation of mechanically acceptable functional replacement cartilage and ligament tissue, and that the replacement tissue will give rise to a flexible open structure without substantial loss of voice or sphincter activity.

Example 5

The efficacy of OP-1 in regeneration of dog larynx was examined by treating thyroid cartilage defects with thyroid allografts covered with host perichondrium. Prior to implantation, allografts were frozen, thawed and demineralized. Animals were sacrificed 4 months following surgery. Macroscopic examination of all specimens was done by a laryngeal surgeon and no pathological changes was observed in any of the neck areas of the sacrificed animal. No pathological ossification was found in surrounding muscles and other connective structures. Also, no changes were found in the inner part of the larynx itself, including all three laryngeal compartments, namely, vestibulum, cavum laryngis and cavum infraglotticum.

Eleven specimens from 11 animals were analyzed, including: (i) 3 specimens from control dogs implanted only with allografts (Group I), (ii) 4 specimens from dogs whose implants were coated with 500 µg OP-1 and placed under the perichondrium of the host thyroid cartilage (Group II); (iii) 2 specimens from dogs whose implants were coated with 500 µg OP-1 and placed under the neck fascia of the host thyroid cartilage (Group III); and (iv) 2 specimens from dogs whose allograft implants had been extracted with salt and guanidinium hydrochloride, coated with 500 µg OP-1 and placed under the perichondrium of the host thyroid lamina (Group IV).

Upon termination, larynx and the surrounding structures were removed, inspected and fixed in 10% formalin for 48 hours. Then the left thyroid lamina containing the repaired defect was dissected out and post-fixed in 4% paraformaldehyde. Each thyroid lamina was divided into 4 blocks covering the entire specimen and each block was individually embedded into plastic. Histological analysis using serial sections throughout the defect that were separated by approximately 1-2 mm was then performed.

Group I: Control Allograft Implants

In this control group, dried implants were not exposed to any solution prior to implantation. All the implants were sutured in a way that the edge was overlapping the host defect site by approximately 2 mm.

In none of the three control specimens was new bone or cartilage formation observed. Moreover, the entire allografts remained completely intact with no apparent reduction in size. No resorption, new vascularization or inflammation was observed. In one dog the implanted allograft slipped laterally because of failed sutures and the defect was closed by irregular fibrous connective tissue.

Group II: Implants Coated with OP-1 and Covered with Host Perichondrium

In these dogs, the closed defects appeared hard and stable upon mechanical (finger) compression. It was not possible to shift the defect area by intensive palpation, indicating that the implants resisted regular mechanical strains at the implantation site. These strains included compression of soft tissues (muscles, fascias, etc.) during swallowing, breathing, and barking. Histological analysis indicated that OP-1 induced bone, cartilage and ligament-like repair of the thyroid cartilage defects. The implanted allograft was not completely resorbed within a 4 month observation time.

Healing at the largest diameter of the defect was particularly examined. On both ends of the large defect site, newly formed cartilage was evident. The new cartilage spanned about 40-50% of the defect area and was completely fused to the host thyroid cartilage. The new cartilage was hyaline cartilage with crossing elastic cartilage fibers.

Young cartilage was observed, accompanied by a definite graduation from mesenchymal cells to chondroblasts to chondrocytes. As mesenchymal cells differentiated into chondroblasts, the latter cells deposited matrix components around themselves, surrounding themselves in their own secretory products. As a result, a small lacuna was formed. The chondroblasts resided within these spaces without any contact with other cells. The matrix was acidophilic. Maturation of the chondroblasts into chondrocytes was accompanied by cellular hypertrophy and a change from lacunar shape to an ovoid or angular configuration.

The allograft matrix was found at a distance from the new cartilage layers, being physically separated by a fibrous tissue layer. No remodeling of the cartilage at the left defect site was observed within the 4 month observation period, indicating that the newly formed cartilage was stable for at least that period. The much smaller amount of cartilage at the right defect site was in contact with a bone layer. The middle and right parts of the defect comprised of the remaining allograft, newly formed bone, and ligament-like structures. The new bone occupied about 20-25% of the defect area. The surfaces of newly formed trabeculi were irregularly covered with active osteoblasts depositing thick osteoid seams. The entire defect site was tightly packed into the connective fibrous tissue. The cartilage and bone surfaces were directly covered with perichondrium and periosteum-like tissue that was highly cellular and vascularized containing the precursor cells.

The defect site was embraced from outside with a ligament-like layer of regular fibrous connective tissue. The significant feature of this connective tissue was the orderly, parallel orientation of collagenous fibers. The fibrocytes delimited the extent of individual bundles, making this tissue a low cellular material. The nuclei of the cells and the fibers had a site-dependent wavy appearance. Such connective tissue is the predominant type that forms tendons and ligaments. As larynx contains ligaments, it is expected to have precursor cells in this particular microenvironment. Individual bundles of these highly organized fibers were held together by loose connective tissue, which is also a characteristic of ligaments and tendons. In addition, reduced vascularity of this tissue was a further marker of the ligaments that account for variable regenerative ability in standard orthopaedic procedures.

In one dog, the implant slipped slightly medially, but remained largely in place. Bone that covered both allograft surfaces was in direct contact with the allograft at the anterior (outer) defect site and at a distance from the allograft at the posterior (inner) defect site. Endochondral bone formation was observed, evidenced by replacement of a cartilage anlage with bone. The allograft split into two pieces separated by a connective fibrous tissue layer. A thick fibrous layer separated also the newly formed bone from the posterior allograft site. Newly formed bone comprised of trabeculi covered with osteoid seams and active cuboid osteoblasts. This indicated that bone induction was not dependent on the rate of allograft removal and that the allograft comprised of type II collagen did not direct the type of tissue formed at the regeneration site.

Group III: Implants Coated with OP-1 and Covered with Neck Fascia

The results in this group of these dogs indicated that using neck fascia, instead of the perichondrium, to cover the implant resulted in a significant delay in new tissue induction and allograft removal.

Group IV: Implants Chemically Extracted, Coated with OP-1 and Covered with Perichondrium In this group of dogs, the closed defects appeared hard and stable upon mechanical (finger) compression and could not be differentiated from those from the Group II animals. Histological analysis indicated that OP-1 induced bone, cartilage and ligament-like repair of thyroid cartilage defects. As in the Group II animals, the process was not completed during a 4 months observation period. However, effective healing of the laryngeal tissue defects was observed.

Healing at the largest diameter of the defect was particularly examined. On both ends of the large defect site, newly formed bone and cartilage were evident. Bone and cartilage occupied about 30-35% and 25-30%, respectively, of the full thickness defect area. The boundary between the host thyroid cartilage and the new bone healed by the formation of a bone continuum, while the boundary between the host thyroid cartilage and the new cartilage by a cartilage continuum. The bone continuum described a complete fusion to the host thyroid cartilage by a microcallus formation mechanism. Namely, adolescent host thyroid cartilage lamina might contain a bone layer covered with two hyaline cartilage layers; by creating a defect during the surgical procedure, the host bone was eventually damaged (fractured); installing the OP-1 coated implant into the defect site induced bone healing by microcallus formation.

In all the specimens and tissue blocks tested, whenever there was bone residing in the thyroid lamina, there was also bone formed at the adjacent defect boundary. This observation suggested that OP-1 attracted precursor cells from the host bone marrow. In contrast, if there was no residing bone in the host thyroid lamina, cartilage continuum developed, connecting the host thyroid to the remaining allograft and/or surrounding ligament-like tissue. In such a way newly formed tissues and the unresorbed allograft composed a very tight regenerating defect site. Newly formed bone extended to the middle of the defect and was localized between unresorbed allograft pieces. It was filled with hematopoietic marrow and fully mineralized. As in the Group II animals, newly formed ligament-like structures were also observed, where ligament bundles attached to the newly formed cartilage and bone.

These results indicated that 500 μg of OP-1 delivered via a thyroid allograft carrier induced regeneration and repair of thyroid lamina cartilage defects, and that the new tissue met the animals' mechanical needs for swallowing, barking and breathing. The new tissue, which included bone, cartilage and ligament-like structures, composed more than 80% of the defect area.

The results further indicated that the healing depended in large part on OP-1 and the surrounding tissues which provided the various precursor cells.

The tissue differentiation in the healing process did not appear to be carrier-dependent, for a Type II collagen carrier did not solely promote new cartilage formation.

These results also suggested that the three types of newly formed tissues and their appendices, e.g., bone marrow, blood vessels, etc., were tightly connected into a "bone-cartilage-ligament continuum" of tissues. Thus, it appeared that OP-1 served as a multiple tissue morphogen in this specific microenvironmen.

Finally, these results indicated that OP-1 was not merely an osteogenic morphogen—it could also induce the formation of permanent cartilage and ligament-like tissues.

Example 6

This example describes another study on the efficacy of osteogenic protein in regenerating new tissue at a defect site. This study contained five experimental groups that were divided into two sub-studies. Groups I-III compared the effects of different OP-1 carriers on the repair of identical thyroid cartilage defects. The tested carriers were CMC, CMC/blood paste, and HELISTAT® sponge (a Type I collagen composition). Groups IV and V addressed different animal models and surgical methods, where larger defects as used in human clinical practice were created and repaired by combinations of OP-1/CMC device, VICRYL™ surgical mesh, and PYROST® (a bone mineral composition) rigid supports. These latter two groups were approximations of the combined product and procedure envisioned for a clinical setting. Surgeries on Groups I-III were performed one or two months before surgeries on Groups IV and V. The experimental protocol is summarized below in Table II.

TABLE II

Dog Larynx Reconstruction Using OP-1

| Group | Dogs | Defect | OP-1 | Duration |
|---|---|---|---|---|
| I | 3 | I | A | 4 months |
| II | 3 | I | B | 4 months |
| III | 3 | I | C | 4 months |
| IV | 3 | II | A | 6 months |
| V | 3 | III | A × 2 | 6 months |

Defect
I: Partial removal of right thyroid lamina. OP-1 was applied to the defect and contained between perichondrial layers adjacent to the thyroid cartilage.
II: Partial vertical laryngoctomy. An OP-1/CMC device was implanted between layers of VICRYL ™ mesh. The implant was fixed to PYROST ® rods, which positioned and shaped the implant. The implant was contained between a pharyngeal mucosa flap (inside) and the perichondrium (outside).
III: Extended partial vertical laryngoctomy. OP-1/CMC devices (2 per animal) were implanted and fixed as described for partial vertical laryngoctomy.
OP-1
A. OP-1/CMC device.
B. OP-1 in CMC/blood paste.
C. OP-1 applied to HELISTAT ®

Analysis of the treated laryngeal tissue indicated that all three formulations (OP-1/CMC device, OP-1/CMC blood paste. OP-1/HeLISTAT®) induced bone and cartilage formation at the defect site. Some implants were partially integrated and others were fully integrated with existing cartilage surrounding the defect sites.

Example 7

Using the protocols described in Examples 1-3, the efficacy of osteogenic protein in generating mechanically acceptable replacement of tracheal hyaline cartilage rings and the annular ligament is demonstrated. A defect sufficient to remove at least ⅔ of one of the several allocating hyaline cartilage rings is created. Donor tracheal allograft matrix is prepared as described above in Example 1. A synthetic polymer matrix can also be used. Preferably, 10-750 kg OP-1 is used. The replacement matrix is coated with the osteogenic protein and surgically implanted between two remaining rings using metal-mini plates.

Animals are monitored by tracheal endoscopy and by manual palpitation. They are sacrificed at 24 weeks following surgery. It is anticipated that full incorporation of the graft will result, and newly induced ligament-like membrane will form and connect the new ring with the neighboring tracheal rings, giving rise to a flexible open tube-like structure with interrupted respiration.

Example 8

The following protocol may be used to determine whether a morphogen such as OP-1 is effective in vivo in promoting regeneration of tissue to repair defects in intervertebral discs.

Intervertebral discs are aseptically harvested from mature dogs, trimmed of all adherent tissue, and devitalized as described in Example 1. Each disc is bisected in the coronal plane and 3 mm full-thickness circular defects are made in each half. The discs are coated with the morphogen and surgically re-implanted. The discs are examined for the extent of repair at the defect sites at various time points after re-implantation.

Example 9

This example demonstrates the efficacy of osteogenic protein in stimulating cartilage matrix repair by cells, specifically nucleus pulposus ("NP") and annulus fibrosus ("AF") cells, isolated from intervertebral discs ("IVDs").

In this example, lumbar discs were isolated from New Zealand White rabbits and NP tissue was separated from AF tissue by dissection. NP and AF cells were separately isolated from the two tissues by sequential enzyme digestion and re-suspended in 1.2% low viscosity sterile alginate, which was then formed into beads by expression through a 22 gauge needle into a 102 mM $CaCl_2$ solution. The beads were separately cultured in DMEM/F-12 medium containing 10% fetal bovine serum ("FBS"), 25 µg/ml ascorbate and 50 µg/ml gentamycin. The medium was changed daily.

After 14 days, each culture was subdivided into three groups. The first group was a control group cultured for 12 more days. The second and third groups were subjected to chemo-nucleolysis for 2 hours by 0.1 U/ml chondroitinase ABC ("C-ABC"), which is commonly used to degrade the chondroitin sulfate and dermatan sulfate chains of proteoglycans ("PGs"). Proteoglycans are a necessary component of the extracellular matrix of IVDs. Low levels of PGs are associated with degenerative disc disease. It is believed that reduced PG synthesis plays a contributory role in disc degeneration. The second and third groups were subsequently cultured for 12 days, the second group in the presence of 200 ng/ml of OP-1, the third group in the absence of OP-1.

Assays were performed on all three groups immediately after the C-ABC treatment, and at 3, 6, 9, and 12 days afterwards. The rate of mitosis was determined by measuring the amount of DNA using the Hoechst 33258 dye and fluorometry. The amount of sulfated PG synthesis was measured using the DMMB dye assay described in Hauselmann et al., *J. Cell Sci.* 107:17-27 (1994), the teachings of which are herein incorporated by reference.

The cells of the second group cultivated in the presence of OP-1 re-established a matrix significantly richer in PGs than those of the third group cultivated in the absence of OP-1, as well as the first control group. These results show the osteogenic protein can stimulate growth of the extracellular matrix.

Example 10

This example demonstrates the efficacy of osteogenic protein in stimulating cartilage matrix repair by cells, specifically NP and AF cells, isolated from IVDs.

In this example, lumbar discs were isolated from New Zealand White rabbits and NP tissue was separated from AF tissue by dissection. NP and AF cells were separately isolated from the two tissues by sequential enzyme digestion and re-suspended in 1.2% low viscosity sterile alginate, which was then formed into beads. The cells were separately cultured in DMEM/F-12 medium containing 10% FBS, with the medium being changed daily. After 7 days, each culture was subdivided into three groups. The first group was a control group which was not treated with OP-1. The second and third groups were grown in the presence of OP-1 for 72 hours, the second group being treated with 100 ng/ml of OP-1, and the third group being treated with 200 ng/ml of OP-1. Radiolabeled $^3$H-proline was added to the cultures for the last 4 hours of incubation with OP-1. After the incubation, collagen was extracted from the cultures, and the rate of collagen production was determined by measuring $^3$H-proline's incorporation into the extracts. Collagen production is associated with growth and repair of cartilage matrix. To determine the rate of cell proliferation, the content of each group's DNA was measured using Hoechst 33258 dye.

Osteogenic protein increased collagen production in both NP and AF cell cultures in a concentration-dependent manner. The third group incorporated more radiolabel than the second group, which in turn incorporated more radiolabel than the first control group. Osteogenic protein had a significant mitogenic effect at high concentrations, which accounts for some of the elevation in collagen production. Nonetheless, the rate of collagen synthesis was significantly increased even when increased cell proliferation is accounted for. These results suggest that osteogenic protein stimulates the growth and repair of extracellular matrix.

Example 11

This example illustrates the efficacy of osteogenic protein in stimulating synthesis of cartilage matrix components (e.g., collagen and PGs) by cells, specifically NP and AF cells, isolated from IVDs.

In this example, lumbar discs were isolated from New Zealand White rabbits and NP tissue was separated from AF tissue by dissection. NP and AF cells were separately isolated from the two tissues by sequential enzyme digestion and encapsulated in 1.2% low viscosity sterile alginate beads as described in Chiba et al. *Spine* 22:2885 (1997), the teachings of which are herein incorporated by reference. The beads were separately cultured in DMEM/F-12 medium containing 10% FBS, with the medium being changed daily. After 7 days, each culture was subdivided into three groups. The first group was a control group which was not treated with OP-1. The second and third groups were grown in the presence of OP-1 for 72 hours, the second group being treated with 100 ng/ml of OP-1, and the third group being treated with 200 ng/ml of OP-1.

To provide a marker for collagen synthesis, radiolabeled $^3$H-proline was added to the cultures for the last 16 hours of incubation with OP-1. To provide a marker for PG synthesis, radiolabeled $^{35}$S-sulfate was added to the cultures for the last 4 hours of incubation with OP-1. To provide a marker for cell proliferation, MTT was added to the cultures for the last 60 minutes of incubation with OP-1. Assays were then performed on the cell cultures to measure cell proliferation, PG synthesis and collagen synthesis. Cell proliferation was assayed by lysing and centrifuging the cells and measuring the absorbance of the supernatant at 550 nm, as described in Mossman, *J. Immunol. Methods* 65:55 (1984), the teachings of which are herein incorporated by reference. PG synthesis was determining by measuring incorporation of $^{35}$S into the matrix, as described in Mok et al., *J Biol. Chem.* 269:33021 (1994), and Masuda et al., *Anal. Biochem.* 217:167 (1994), the teachings of which are herein incorporated by reference.

Collagen synthesis was assayed by measuring incorporation of $^3$H-proline into the matrix, as described in Hauselmann et al., supra.

The data showed that OP-1 elevated synthesis of both PG and collagen in both NP and AF cultures in a concentration-dependent manner. The third group incorporated more of both kinds of radiolabel than the second group, which in turn incorporated more of both kinds of radiolabel than the first control group. Osteogenic protein had a significant mitogenic effect at high concentrations, which accounted for some of the elevation in collagen and PG production. Nonetheless, the rate of collagen and PG synthesis was significantly increased even when increased cell proliferation was accounted for. These results suggest that osteogenic protein stimulates the growth and repair of extracellular matrix.

Example 12

The in vivo effects of OP-1 on the repair of intervertebral discs are studied in two rabbit models—one model involves stab-wounding of the annulus fibrosus, as described in Lipson et al., *Spine* 6:194 (1981), and the other model involves intradiscal C-ABC injection, as described in Kato et al., *Clin. Orthop.* 253:301 (1990).

Briefly, for the stab-wounding method, an incision will be made in the annulus fibrosus of New Zealand White rabbits. Each rabbit will have two discs treated: one disc treated with OP-1 and the other treated with saline. For the intradiscal injection model, the lumbar discs of New Zealand White rabbits will be exposed and C-ABC in the presence and absence of OP-1 will be injected into the intervertebral discs. At varying times following treatment, the rabbits will be euthanized and the effects of OP-1 on the repair of the intervertebral disc space will be evaluated by methods well known in the art. These methods include magnetic resonance imaging, mechanical tests, histological analysis, and biochemical studies of the various extracellular matrix components in the repaired discs.

Example 13

This example describes another study on the regeneration of dog larynx with OP-1 and different carriers.

In this study, three different osteogenic devices were used to deliver OP-b 1. They were the OP-1/CMC device, OP-1/CMC/blood paste, and OP-1/HELISTAT® sponge. The blood paste device was prepared by mixing 160 µl OP-1 at 5 mg/ml with 400 µl 20% CMC via a syringe connection, followed by addition of 240 µl freshly drawn autologous blood and continuous mixing. The final volume applied to the defect was 0.8 ml. The HELISTAT® device was prepared by applying 225 µl OP-1 onto 6 mg HELISTAT® sponge for every 2 cm$_2$ defect area.

Three different treatment methods were studied. In the first treatment method. defects in the left thyroid cartilage lamina were created as described above; OP-1 devices were applied to the defect areas and maintained between perichondrial layers adjacent to the defect. in the second treatment method, partial vertical laryngoctomy was initially performed, and the OP-1/HELISTAT® device was implanted; immobilization of the reconstructed area was achieved with PYROST® as described in Example 6; the implant was placed between a pharyngeal mucosal flap (inside) and the perichondrium (outside). The third treatment method involved anterior cricoid split and luminal Augmentation; in this method, the OP-1/HELISTAT® device was implanted and immobilized with PYROST®.

During the course of experiment, the test animals had no recorded breathing, eating and barking problems. Dogs were killed four months following surgery and all specimens, including large reconstructed areas, appeared hard upon palpation. Dissection of the larynx was performed, with special care not to disturb incompletely healed areas, if any. Specimens were cut and embedded into plastics as previously described.

Group I: OP-1/CMC

This group of animals were treated with the first treatment method, supra, using the OP-1/CMC device. Thyroid defects in all three dogs healed almost completely. Surprisingly, although CMC might have been too liquidy, the newly induced tissue was nicely positioned within the defect margins. This observation suggested that the closure with soft tissue was successfully performed. This was also the first evidence that CMC could serve as a carrier for OP-1. Moreover, although there was no evidence that OP-1 remained within CMC for a longer period of time being protected against proteolytic degradation, the newly induced bone was well incorporated into the defect. Unlike the above dog study where OP-1 applied with an allograft matrix could induce bone, cartilage and ligament, this study showed that only bone and ligament were formed. The new bone was well connected to both cartilage ends and embraced by a ligament-like soft tissue. Von Kossa staining indicated complete mineralization of the new bone. Abundant bone marrow filled the ossicle almost completely. Remnants of cartilage anlage were found. Bone surfaces were covered with very active osteoblasts, which were accumulating a thick layer of osteoid along the bone surfaces. The cortical bone outside the newly formed ossicle was undergoing intensive remodeling, as indicated by intracortical bone remodeling units filled with osteoclasts, osteoblasts and blood capillaries. At several cartilage-bone boundaries, the process of endochondral bone formation was still active, although the border between the two tissues was not clearly demarcated. This result indicated that a new layer of cartilage which formed between old cartilage and new bone would ossify in time, and that newly formed cartilage was only transiently present and thus, lacked the characteristics of a permanent tissue.

In the dog study described in Example 5, cartilage allografts were used as carriers for OP-1; the newly formed cartilage was separated from the bone and appeared permanent. However, in this study, where a different carrier (CMC) was used and the tissue formation was not controlled by the slow release of morphogen or guided by an extracellular matrix carrier, osteogenesis prevailed over chondrogenesis. This result suggested that precursor cells recruited for tissue formation in both the previous and present studies came from the same cellular pool, and that the morphogen threshold in the presence of CMC promoted osteogenesis. In other words, the carrier material and the morphogen contained therein coordinately influenced the outcome of tissue differentiation. Further, in Example 5, the allograft carriers were not completely removed by resorption within the 4 month observation period. Here, where CMC carriers were used, the rate of the healing was significantly faster, for the entire defect area was closed and almost completely remodeled within the same period of time.

Group II: OP-1/CMC/Blood

This group of animals were treated with the first treatment method, supra, using the OP-1/CMC/Blood device. The defects in all dogs healed completely. As in the Group I dogs, bone and ligament tissues were induced, while no new cartilage was apparent. The newly formed tissues were nicely positioned within the defect margins. Addition of blood to CMC seemed to have created more new bone that was undergoing intracortical bone remodeling. The remodeling resulted in islands of new bone marrow with broad osteoid seams. The new bone was well connected to both cartilage ends and embraced by a ligament-like soft tissue. Von Kossa staining indicated complete mineralization of the new bone. Bone surfaces were covered with active osteoblasts accumulating a thick layer of osteoid along the surfaces. The margins where the old cartilage and the new bone merged were sharply separated by a thin layer of well organized connective tissue. No signs of endochondral bone formation were detected within the old cartilage, suggesting that the process of classification was faster in defects treated with the OP-1/CMC/blood device than in defects treated with the OP-1/CMC device. The presence of osteogenic precursors present in the blood could have accounted for this difference.

Group III: OP-1/HELISTAT®

This group of animals were treated with the first treatment method, supra, using the OP-1/HELTSTAT® sponge device. The defects in all dogs healed completely by the formation of new bone. Unlike the Group I and II dogs, the Group III dogs contained less ligament-like tissue at the healed defect sites. In one animal, the new tissue was nicely positioned within the margins and only a small amount protruded laterally. In other animals, the new tissue formed multiple layers; in one dog the new tissue was completely out of the defect frame, inducing bone formation in the adjacent area.

The abundance of ossification was determined by the size and positioning of the HELISTAT® sponge. Margins of the new bone and the old cartilage were separated by a thin fibrous layer. Small amounts of collagen from the HELISTAT® sponge remained unresorbed. Dislocation of the sponge in one animal led to abundant bone formation outside the defect site. The orientation of bone trabeculi followed the path of collagen fibers within the sponge, suggesting that the ossification was guided by the carrier matrix to which the morphogen had been bound. The decrease in the amount of ligament-like tissue observed, in this group of animals was likely due to the lesser ability of Type I collagen to attract ligament precursor cells.

Group IV: Partial Vertical Laryngoctomy

This group of animals were treated with the second treatment method, supra, using the OP-1/HELISTAT® sponge device. The anterior half of the left thyroid lamina and the surrounding soft tissues. (ventricular and vocal folds) were surgically removed. Immobilization of the reconstructed area was performed with PYROST®. The implant was placed between a pharyngeal mucosal flap (inside) and the perichondriurn (outside). Regeneration of the larynx skeleton was still in progress with bone filling in the removed thyroid cartilage, as of 4 months post-operation. The new bone was still undergoing remodeling and provided a good scaffold for the larynx skeleton integrity. The gap between the vocal and thyroid cartilages was filled with unorganized connective tissue. allowing normal air flow.

Group V: Anterior Cricoid Split with Luminal Augmentation

This group of animals were treated with the third treatment method, supra, using the OP-1/HELLSTAT® sponge device. The anterior part of the cricoid arcus was transected and a lumen extension was created by external implantation of PYROST®. The space between the cricoid ends was filled with the OP-1/HELISTAT® device. The lumen remained extended while the PYROST® was partially removed or powdered and integrated with the new bone. The central area was occupied by new bone that was undergoing active remodeling. Surprisingly, minimal bone tissue was formed adjacent to the PYROST®, which might have served as an affinity matrix for the OP-1 protein released from the adjacent HELISTAT® sponge. In one specimen, the new bone and PYROST®-surrounded bone formed an extended bone area that did not compromise the lumen diameter. No ligament-like tissue was formed, indicating the lack of precursor cells in the vicinity of the cricoid cartilage.

What is claimed is:

1. A method for repairing a defect in an intervertebral disc comprising the step of administering to the disc an effective amount of a composition comprising an osteogenic protein selected from the group consisting of OP-1 (osteogenic protein-1), OP-2, OP-3, BMP-2 (bone mohogenic protein-2), BMP-3, BMP-4, BMP-5, BMP-6, BMP-9, BMP-10, BMP-11, BMP-15, BMP-3B, DPP (decapentaplegic protein), Vg-1 (vegetal protein-1), Vgr-1 (murine vegetal protein-1), 60A protein, GDF-1 (growth differentiation factor-1), GDF-2, GDF-3, GDF-5, GDF-6, GDF-7, GDF-8, GDF-9, GDF-10 and GDF-11.

2. The method of claim 1, wherein the composition is administered to the disc by intradiscal injection.

3. The method of claim 1, wherein the composition comprises a liquid carrier.

4. The method of claim 3, wherein the composition comprises a solution or a suspension of the osteogenic protein in the liquid carrier.

5. The method of claim 3, wherein the liquid carrier is an acetate buffer, a citrate buffer or phosphate-buffered saline.

6. The method of claim 3, wherein the liquid carrier is a vegetable oil.

7. The method of claim 1, wherein the osteogenic protein is OP-1.

8. The method of claim 1, wherein the osteogenic protein is GDF-5.

9. The method of claim 1, wherein the osteogenic protein is GDF-6.

10. The method of claim 1, wherein the osteogenic protein is BMP-2.

11. The method of claim 1, wherein the osteogenic protein is BMP-4, BMP-5 or BMP-6.

12. The method of claim 1, wherein the composition comprises a paste or gel carrier.

* * * * *